US012184076B2

(12) United States Patent
Kikkawa

(10) Patent No.: US 12,184,076 B2
(45) Date of Patent: Dec. 31, 2024

(54) GREEN ENERGY TRANSPORTATION SYSTEM AND ENERGY TRANSPORTATION METHOD

(71) Applicant: Yoshitsugi Kikkawa, Yokohama (JP)

(72) Inventor: Yoshitsugi Kikkawa, Yokohama (JP)

( * ) Notice: Subject to any disclaimer, the term of this patent is extended or adjusted under 35 U.S.C. 154(b) by 0 days.

(21) Appl. No.: 18/632,563

(22) Filed: Apr. 11, 2024

(65) Prior Publication Data
US 2024/0372370 A1 Nov. 7, 2024

(30) Foreign Application Priority Data

Apr. 11, 2023 (JP) .................................. 2023-064400

(51) Int. Cl.
| | | |
|---|---|---|
| *H02J 3/38* | (2006.01) | |
| *B63B 17/00* | (2006.01) | |
| *B63B 25/08* | (2006.01) | |
| *C07C 1/04* | (2006.01) | |
| *C07C 7/04* | (2006.01) | |
| *C25B 1/04* | (2021.01) | |
| *C25B 9/09* | (2021.01) | |
| *C25B 15/08* | (2006.01) | |

(52) U.S. Cl.
CPC .......... *H02J 3/381* (2013.01); *B63B 17/0036* (2013.01); *B63B 25/08* (2013.01); *C07C 1/041* (2013.01); *C07C 7/04* (2013.01); *C25B 1/04* (2013.01); *C25B 9/09* (2021.01); *C25B 15/081* (2021.01); *H02J 2300/10* (2020.01)

(58) Field of Classification Search
CPC .......... H02J 3/38; H02J 3/381; H02J 2300/10; C25B 15/08; C25B 15/081; C25B 1/04; C25B 9/09; B63B 17/00; B63B 17/0036; B63B 25/08; C07C 1/041; C07C 7/04
See application file for complete search history.

(56) References Cited

FOREIGN PATENT DOCUMENTS

| | | | |
|---|---|---|---|
| JP | H11-241618 | A | 9/1999 |
| JP | 2011-235675 | A | 11/2011 |
| JP | 2015-064022 | A | 4/2015 |
| JP | 2016-154411 | A | 8/2016 |
| JP | 2017-176954 | A | 10/2017 |
| JP | 2019-103153 | A | 6/2019 |
| JP | 2023-041049 | A | 3/2023 |

*Primary Examiner* — Robert L Deberadinis
(74) *Attorney, Agent, or Firm* — Locke Lord LLP

(57) ABSTRACT

To provide a transportation system that can transport renewable energy from a power generation facility to an energy consumption location. The system consists of a power generator that generates and stores electricity from a renewable energy, a hydrogen generator that generates hydrogen by electrolysis of water using electricity obtained from the power generator, a methane synthesizer that generates methane by the Sabatier reaction using the hydrogen and a recycled $CO_2$ as raw materials, and a methane transportation system that transports the methane without emitting $CO_2$ to the atmosphere, a methane transportation system that transports the methane without emitting $CO_2$ into the atmosphere, a power generation and carbon capture unit that generates electricity by reacting the transported methane with oxygen and captures $CO_2$ discharged during the power generation as recycled $CO_2$, a $CO_2$ transportation system that transports the recycled $CO_2$ to the methane synthesis site without emitting $CO_2$ to the atmosphere.

20 Claims, 17 Drawing Sheets

Values in parentheses ( ) indicate energy efficiency

*1: When PEM is used for electrolysis, the total energy efficiency of M2 and M3 is 61%; when SOEC is used for electrolysis, the total energy efficiency of M2 and M3 is 88%.

*2: when GTCC is used for power generation

| Stream property Stream No. Name | ① Liquefied methane | ② Methane gas | ③ Highly concentrated CO₂ | ④ Liquefied CO₂ |
|---|---|---|---|---|
| --Overall-- | | | | |
| Molar flow rate kmol/s | 1 | 1 | 1 | 1 |
| Mass flow rate kg/s | 16.043 | 16.043 | 44.01 | 44.01 |
| Temperature C | -162 | 17.8866 | 30 | -46 |
| pressure bar | 50 | 49.5 | 65 | 64.5 |
| Vapor mol fraction | 0 | 1 | 1 | 0 |
| Enthalpy MJ/s | -89.471 | -75.935 | -397.73 | -411.27 |
| Tc C | -82.52 | -82.51 | 31.05 | 31.05 |
| Pc bar | 46.0015 | 46.0015 | 73.8152 | 73.8152 |
| Std.sp gr. wtr =1 | 0.3 | 0.3 | 0.827 | 0.827 |
| Std.sp gr. air =1 | 0.554 | 0.554 | 1.52 | 1.52 |
| Degree API | 340.1666 | 340.1666 | 39.6004 | 39.6004 |
| Average mol wt | 16.043 | 16.043 | 44.01 | 44.01 |
| Actual dens kg/m³ | 424.8002 | 36.8315 | 212.1146 | 1140.8703 |
| Actual vol m³/h | 135.9576 | 1568.0917 | 746.936 | 138.8729 |
| Std.liq m³/h | 192.5163 | 192.5163 | 191.5795 | 191.5795 |
| Std vap 0 C m³/h | 80689.133 | 80689.133 | 80689.133 | 80689.133 |

LCO2 cargo tanks
(Independent Type C tanks)

Values in parentheses ( ) indicate energy efficiency
*1:When PEM is used for electrolysis, the total energy efficiency of M2 and M3 is 61%; when SOEC is used for electrolysis, the total energy efficiency of M2 and M3 is 88%.
*2:when GTCC is used for power generation

GREEN ENERGY TRANSPORTATION SYSTEM AND ENERGY TRANSPORTATION METHOD

TECHNICAL FIELD

The present invention relates to a green energy transportation system and a green energy transportation method.

BACKGROUND ART

With growing concern about global environmental issues, the use of so-called renewable energy is increasing as a substitute for finite fossil fuels such as oil, coal, and liquefied natural gas (hereinafter referred to as LNG) and as a measure to mitigate global warming. The renewable energy is renewed in natural phenomena represented by wind, solar, solar thermal, geothermal, hydraulic power, wave power, biomass, etc., and power generation systems using one or more of these types of energy have been proposed.

For example, Patent Literature 1 discloses a wind power generation system including a wind power generator connected to an electric power system so as to generate wind power, an energy storage device connected to the electric power system so as to charge and discharge the power generated by the wind power generator, and a power generation controller that controls power generation of the wind power generator as well as controls charge and discharge of the energy storage device. In this wind power generation system of Patent Literature 1, the power generation controller includes: a system information acquiring unit that acquires a system information indicating the state of the electric power system; a status information acquiring unit that acquires a power generation status information pertaining to the wind power generator and a storage status information pertaining to the power storage device; an information generating unit that generates a power generation plan information pertaining to a power generation plan and a variation range correlation information correlated to the variation range of the power generation plan; and an information transmitting unit that transmits the power generation plan information and the variation range correlation information generated by the information generating unit to a power provider that operates the power system. Based on the system information acquired by the system information acquisition unit and the power generation status information and storage status information acquired by the status information acquisition unit, a power generation output of the wind power generator and a charging/discharging of the energy storage device are controlled. This enables integrated operation of wind-generated power and the power system, thereby contributing to a stable operation of the power system.

Patent Document 2 discloses a power generation system by a renewable energy that generates electricity by a combination of a first power generation facility consisting of a solar power generation facility and a second power generation facility consisting of a wind power generation facility. Patent Literature 2 describes that the power generation system includes a total output controller that calculates a first output upper limit of the second power generation facility based on an interconnection approval amount and an amount of power generated by the first power generation facility, an upper limit re-setting operator that calculates a second output upper limit of the second power generation facility based on the first output upper limit and a current amount or an amount of change of power generation of the second power generation facility, and a controller that sends the second output upper limit to the second power generation facility and controls the power generation of the second power generation facility upon receiving the second output upper limit. This makes it possible to prevent the output of the power generation system from exceeding the interconnection approval amount and to prevent the amount of power generation of the solar power generation facility and wind power generation facility from significantly falling below the interconnection approval amount.

CITATION LIST

Patent Literatures

Patent Literature 1: JP 2016-154411 A
Patent Literature 2: JP 2019-103153 A

SUMMARY OF INVENTION

Technical Problem

However, those renewable energy power generation facilities represented by the wind power and the solar power etc. are often installed in polar regions and desert regions, which are generally remote from densely populated urban and suburban energy consumption areas in considerations of natural conditions such as wind conditions, land costs, social impacts, etc. Therefore, there is a need of transportation technologies for a renewable energy to efficiently transport the energy from such remote locations to energy-consuming areas at low cost. In addition, it is important to reduce the emission of carbon dioxide, which is one of the causes of global warming due to the greenhouse effect, during the energy transportation in order to promote the spread of a renewable energy. In light of the above circumstances, it is an object of the present invention to provide a transportation system and a transportation method that can efficiently transport a renewable energy with low environmental impact from its power generation facilities in remote areas to energy consumption areas.

Solution to Problem

In order to achieve the above object, the present invention is directed to a green energy transportation system including: a power generator that generates and stores electricity from a renewable energy; a hydrogen generator that generates hydrogen by electrolysis of water using the electricity obtained from the power generator; a methane synthesizer that generates methane by a Sabatier reaction using the hydrogen generated by the hydrogen generator and a recycled $CO_2$ as raw materials; a methane transportation system that transports the methane generated in the methane synthesizer to an energy consumption site without emitting $CO_2$ into an atmosphere; a power generation and carbon capture unit that generates electricity by reacting the methane transported by the methane transportation system with oxygen, and recovers carbon discharged during the generation of electricity as recycled $CO_2$; and a $CO_2$ transportation system that transports the recycled $CO_2$ to a methane synthesis site where the methane synthesizer is installed without emitting CO-into an atmosphere.

The present invention is also directed to a green energy transportation method including: a power generation step that generates and stores electricity from a renewable energy; a hydrogen generation step that generates hydrogen by electrolysis of water using the electricity obtained from the power generation unit; a methane synthesis step that generates methane by a Sabatier reaction using the hydrogen generated by the hydrogen generation step and a recycled $CO_2$ as raw materials; a methane transportation step that transports the methane generated in the methane synthesis step to an energy consumption site without emitting $CO_2$ into an atmosphere; a power generation and carbon capture step that generates electricity by reacting the methane transported by the methane transportation step with oxygen, and recovers carbon discharged during the generation of electricity as recycled $CO_2$; and a $CO_2$ transportation step that transports the recycled $CO_2$ to a site where the methane synthesis step is performed without emitting $CO_2$ into an atmosphere.

Advantageous Effects of Invention

According to the present invention, it is possible to efficiently transport a renewable energy to an energy consumption site from its power generation facilities in remote areas with low environmental impact.

DESCRIPTION OF EMBODIMENTS

1. First Embodiment (Tanker Transportation System)

1-1 Green Energy Transportation System

Figure 1:
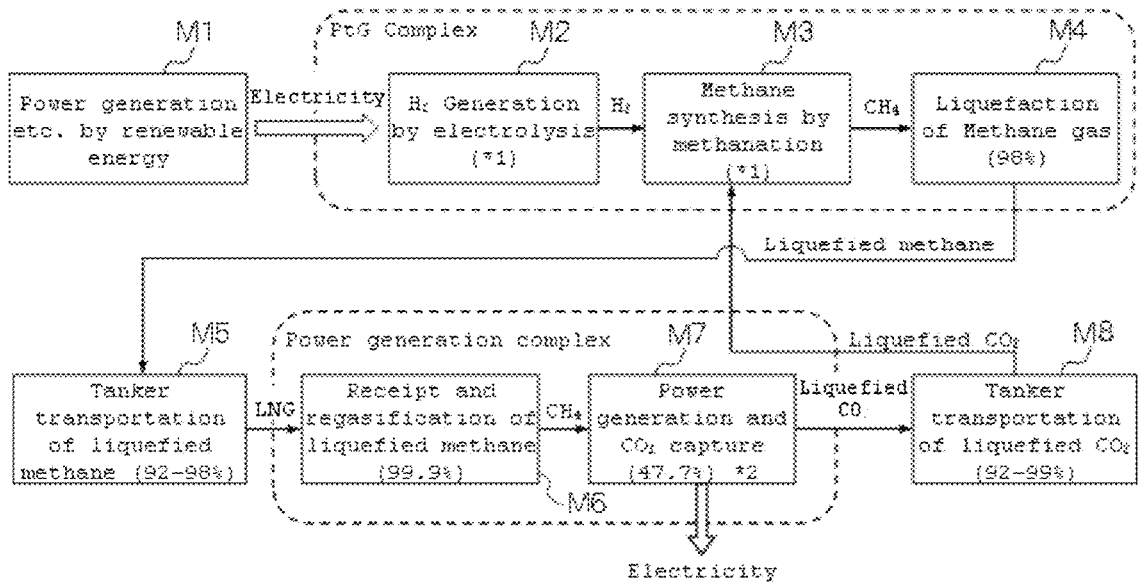
FIG. 1 shows a block flow diagram of the energy transportation system of the first embodiment of the present invention.

Hereinbelow, a first embodiment of the green energy transportation system using a renewable energy as an energy source will be described. As shown in FIG. 1, the energy transportation system of the first embodiment of the present invention includes a power generator M1 that generates and stores electricity from a renewable energy, a hydrogen generator M2 that generates hydrogen by electrolysis of water using the electricity obtained from the power generator M1, a methane synthesizer M3 that generates a methane by methanation through a Sabatier reaction using the hydrogen generated by the hydrogen generator M2 and a recycled $CO_2$ as raw materials, a methane liquefaction unit M4 that liquefies the methane produced by the methane synthesizer M3 into a liquid methane using a rotary positive displacement type refrigerant compressor driven by a synchronous motor to which electricity from the renewable energy as an energy source is supplied via a variable speed motor inverter so as to transport the methane in the form of liquid methane, a methane transportation system M5 that transports the liquefied methane liquefied by the methane liquefaction unit M4 to an energy consumption site without emitting $CO_2$ into the atmosphere, a liquefied methane receiving and regasifying unit M6 that regasifies the liquid methane transported by the methane transportation system M5 after receiving it into a liquefied methane storage tank, a power generation and carbon capture unit M7 that generates electricity by reacting the regasified methane as a raw material after temporarily received in the liquefied methane receiving and regasifying unit M6 with oxygen, and recovers a carbon from the exhaust gas discharged during the power generation in the form of recycled $CO_2$ consisting of highly concentrated $CO_2$ gas, and a $CO_2$ transportation system M8 that transports the recycled $CO_2$ recovered by the power generation and carbon capture unit M7 to the methane synthesis site with the methane synthesizer M3 without emitting $CO_2$ into the atmosphere.

The methane transportation system M5 transports liquefied methane liquefied by the methane liquefaction unit M4 to the energy consumption site by a liquefied methane tanker driven by a first power unit without $CO_2$ emissions to the atmosphere. The power generation and carbon capture unit M7 has a $CO_2$ liquefaction unit that liquefies the recovered recycled $CO_2$ for transportation in the form of liquid $CO_2$. The methane synthesizer M3 has a liquefied $CO_2$ receiving and regasifying unit that regasifies liquefied $CO_2$ transported by the liquefied $CO_2$ transportation system M8 after receiving it in a liquefied $CO_2$ storage tank. In this case, the $CO_2$ transportation system M8 transports the liquefied $CO_2$ obtained by the $CO_2$ liquefaction unit to the methane synthesis site where the methane synthesizer M3 is installed by using a liquefied $CO_2$ tanker that is driven by a second power unit without $CO_2$ emissions to the atmosphere. The values shown in parentheses in FIG. 1 are energy efficiencies. In the case where the location of the wind power farm and the combined cycle are 3,000 nautical miles apart, the energy efficiency is about 25% when the PEM is used for the electrolysis unit, and about 39% when the SOEC is used for the electrolysis unit.

Of the above series of equipment and systems, the hydrogen generator M2, the methane synthesizer M3, and the methane liquefaction unit M4 are sometimes collectively referred to as the PtG Complex (Power to Gas Complex), and the liquefied methane receiving and regasifying unit M6 and the power generation and carbon capture unit M7 are sometimes collectively referred to as the power generation complex. The energy transportation system of this first embodiment of the present invention can use a number of existing infrastructure facilities such as shipping terminals, LNG tankers, and receiving terminals for LNG which are used in Japan and around the world as fuel for power generation or city gas for household use, and therefore the hurdle to realize this green energy transportation system as an alternative energy source of fossil fuels will not be high. Hereinbelow, each of the devices and systems that constitutes the green energy transportation system will be described in detail.

Unlike energy generated by combustion of fossil fuels such as oil, coal, and natural gas, the power generator M1 handles a renewable energy that can be used repeatedly because it is derived from natural phenomena on the earth. Typical renewable energies include wind power, photovoltaic power generation, solar thermal power generation, geothermal power generation, hydroelectric power generation, biomass power generation, wave/tidal-current/tidal power generation, etc. Electricity generated by these renewable energies can be transmitted through AC power cables which are most commonly used.

A generation method of the wind power uses force of the wind to rotate a wind turbine, and its rotational motion is transmitted to a generator to generate electricity. A generation method of the photovoltaic power uses solar cells composed of semiconductors or dyes that is irradiated with sunlight to directly convert light energy into electricity. A generation method of the solar thermal power uses a reflector that concentrates sunlight, and heat of this concentrated sun light generates a high-temperature steam which rotates a turbine for electric generation. A generation method of the geothermal power uses steam, produced from rainwater that has percolated underground and heated by magma, to rotate a turbine for electric generation. A generation method of the hydroelectric power uses a force of falling water stored in a dam to rotate a turbine for electric generation. A generation method of the biomass power uses biomass fuels for combustion that are made by recycled organic resources derived from plants and animals other than fossil fuels, such as unused wood resources, sewage sludge, and general waste, such that steam generated by a combustion heat is used to rotate turbine for electric generation. Wave power generation, tidal-current power generation, and tidal power generation all use ocean energy for power generation. Wave power generation using wave energy can be broadly classified into the following types. Namely, a first type rotates a turbine by using air currents generated by a vertical movement of the sea surface in an air chamber. A second type uses wave energy that is converted into hydraulic pressure via a movable body so as to generate electricity using a hydraulic motor. A third type uses a drop (height) of a sea water discharged from a water storage pond to the sea level so as to rotate a turbine for electric generation where the water storage pond stores the sea water originated from an overflow of sea waves. A generation method of the tidal-current power uses a kinetic energy of tidal-current to rotate a turbine for electric generation. A generation method of the tidal power uses a difference in tidal level caused by tides to rotate a turbine for electric generation which is similar to a hydropower generation.

The power generator M1 can use any of the above-described renewable energies as an energy source, but in the following description, the power generator M1 using the wind power as the energy source for electric generation will be exemplarily described. The wind power can stably generate electricity throughout the day and night, and therefore it is suitable for using existing LNG infrastructure facilities, unlike solar photovoltaic and solar thermal power generation which cannot generate electricity at night. According to an article by Cristina L. Archer et al. (Journal of Geophysical Research, Vol. 110, D12110, doi: 10.1029/2004JD005462, 2005), the potential for wind power is estimated to have about five times the world's entire energy demand. If all the energy needed by mankind is supplied from renewable energies, the concentration of carbon dioxide in the atmosphere can be returned to pre-industrial levels, which may suppress the progression of global warming and bring back to the cold weather of the pre-industrial era.

Figure 2:
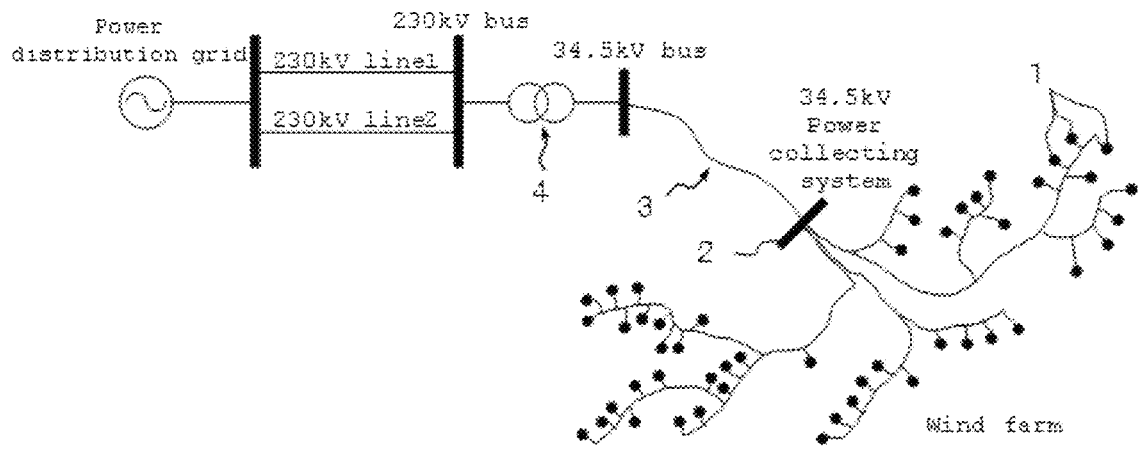
FIG. 2 shows a configuration diagram of a specific example of a power generator that constitutes the energy transportation system of the first embodiment of the present invention.

When the wind power is used as a renewable energy source, it is preferable to operate it as a single power plant as a whole by installing a plurality of wind turbine generators to take advantage of economies of scale, and this type of operation is sometimes referred to as a wind farm. As shown in FIG. 2, for example, a wind farm consists of a plurality of wind power generators (wind turbine generators) 1 with a rated output of 2.5 MW and an output voltage of AC 690 C which are installed offshore along the coast or at a remote location more than about 40 km away. Each output power of the wind turbine generators is boosted to 34.5 kV medium voltage (MV) by pad-mounted or nacelle transformers on the generator side, and then collected in the power collection system 2 and transmitted to the substation 4 via underground or submarine transmission lines 3. At the substation 4, the output power is boosted to a high voltage (HV) of 69 kV or higher for transmission, which is the power transmission level.

The types of the above-described wind turbine generators can be broadly classified into a fixed-speed wind turbine using cage-type induction generator (SCIG) or a variable-speed wind turbine using a doubly fed induction generator (DFIG) or a permanent magnet synchronous generator (PMSG). Among these, the variable-speed wind generator is preferable because it is connected to the grid using a power converter and thus can control the generator speed independently of the grid frequency, and the PMSG is more preferable because it can be gearless by being multi-polarized.

The wind farm can achieve, for example, an output capacity of 15,000 MW by installing 1,000 units of wind turbine generators (V236-15.0 MW) manufactured by VESTAS as shown in Table 1 below, in a substantially matrix pattern.

TABLE 1

| Wind Power Generator | |
|---|---|
| Rated output | 15.0 MW |
| Number of units | 1,000 |
| Rotor diameter (D) | 236 m |
| Separation distance between adjacent generators | |
| Wind direction (7D) | 1,652 m |
| Perpendicular to wind direction (4D) | 944 m |
| Wind Farm | |
| Capacity | 15,000 MW |
| Total length in wind direction | 39,648 m (24 rows) |
| Total width perpendicular to wind direction | 39,648 m (42 columns) |

Figure 3A:
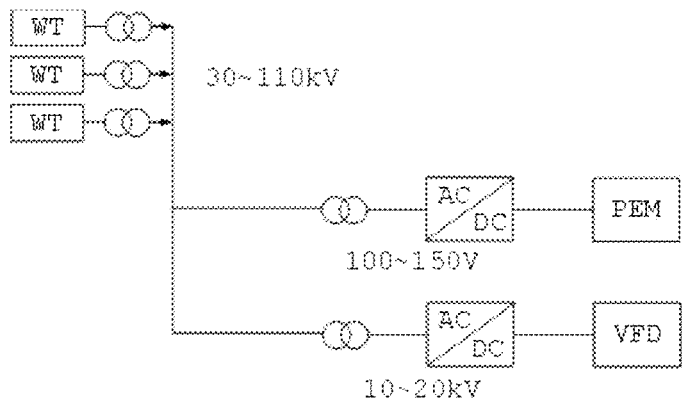
FIGS. 3A and 3B respectively show a conventional power distribution diagram and a specific example of a power distribution diagram in a power generator that constitutes the energy transportation system of the first embodiment of the present invention.

There are two types of power transmission from the wind turbine generator to the substation 4 described above, i.e., AC transmission and DC transmission, which are appropriately selected in consideration of the economy. As shown in FIG. 3A, for example, the power distribution configuration in the case of AC power transmission is as follows: the output voltage of AC 690 V generated by the wind turbine generator (WT) is boosted to 30 to 110 kV by a transformer, and then it is transmitted via a cable of 3-phase AC to a transformer installed near the synchronous motor for driving the refrigerant compressor used in the methane liquefaction unit M4. The output voltage is stepped down by the latter transformer installed near the synchronous motor to 10 to 20 kV and then it is supplied to a VFD (Variable Frequency Drive). Inside the VFD, a DC current converted by an AC-DC converter is converted to AC current of variable frequency by an inverter and this AC current is fed to the synchronous motor. On the other hand, the output voltage is stepped down to 100 to 150 V by a transformer and then it is converted to DC current of 100 to 150 V by an AC-DC converter and this DC current is fed to the electrolyzer for electrolysis of water used in the hydrogen generator M2. For this AC power transmission, the number of the transmission cables are in principle three (3) cables or three (3) sets of two (2) cables.

Figure 3B:
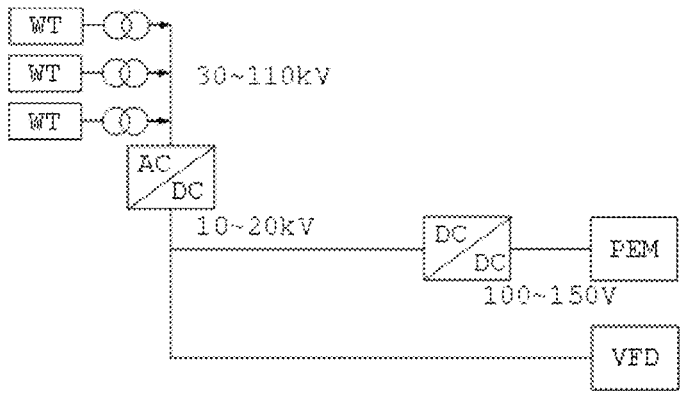
Figure 4:
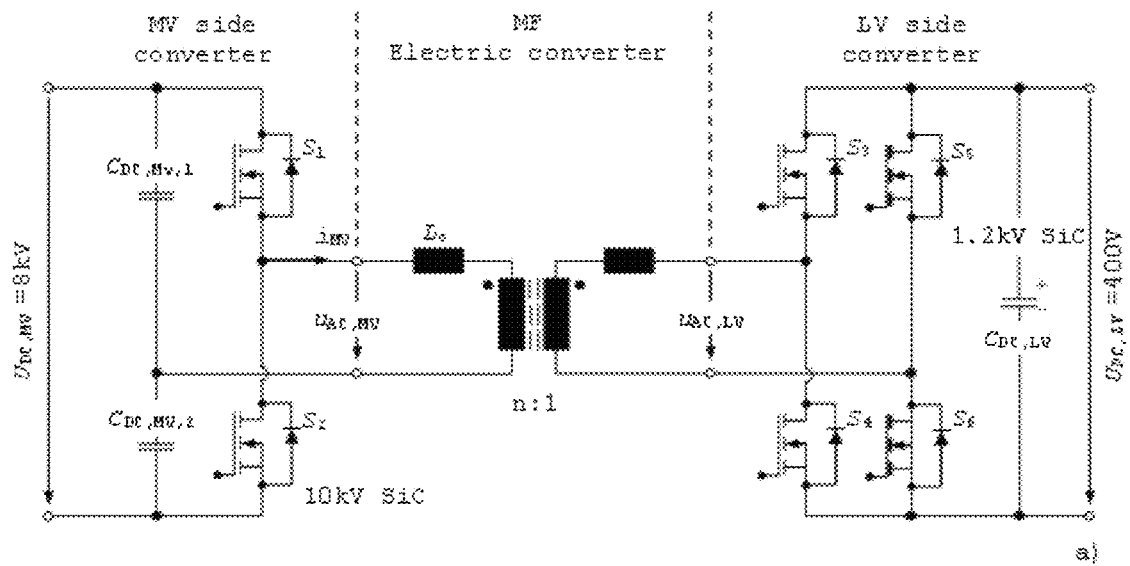
FIG. 4 shows a specific example of a configuration diagram of a solid state transformer (SST) in a power generator that constitutes the energy transportation system of the first embodiment of the present invention.

In contrast, as shown in FIG. 3B, for example, the power distribution configuration in the case of DC power transmission is as follows: the output voltage of AC 690 V generated by the wind turbine generator (WT) is boosted to 30 to 110 kV by a transformer, and then it is converted to a DC power of DC voltage of 10 to 20 kV DC and DC current of 5.0 to 10.0 kA by an AC-DC converter. This DC power is fed to a synchronous motor for driving the refrigerant compressor used in the methane liquefaction unit M4 in the subsequent stage. On the other hand, the voltage of 10 to 20 kV is too high for the electrolyzer for electrolysis of water used in the hydrogen generator M2, and therefore a DC-DC converter consisting of a solid-state transformer (SST), which is suitably used when the degree of step-down is large, as shown in FIG. 4, is used to step down the voltage to 100 to 150 V before feeding. In this DC power transmission, the number of the transmission cable is in principle one (1) cable plus ground cable or two (2) cables. As described above, this configuration of reducing AC power transmission as much as possible and adopting more DC power transmission instead can reduce the transformer and the wiring for 3-phase AC, which leads to cost reduction.

The hydrogen generator M2, located in the subsequent stage of the power generator M1 described above, produces hydrogen by electrolysis of water using the renewable energy obtained by the power generator M1 as an energy source. The hydrogen produced in this way is also referred to as green hydrogen. The apparatus that performs electrolysis of water (also referred to as water electrolysis) can be classified into several types depending on the type of electrolyte, i.e., solid oxide water electrolysis cell apparatus (SOEC), solid polymer water electrolysis apparatus, and alkaline water electrolysis apparatus.

Figure 5:
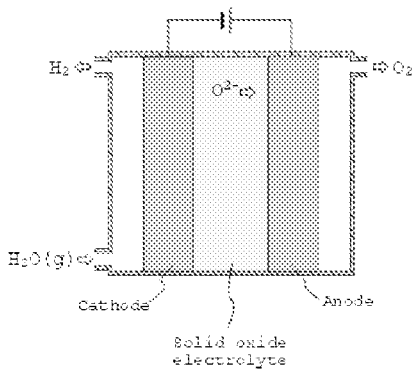
FIG. 5 shows a schematic longitudinal sectional view of a solid oxide water electrolyzer, which is a specific example of a hydrogen generator that constitutes the energy transportation system of the first embodiment of the present invention.

The solid oxide water electrolysis cell apparatus (SOEC) electrolyzes water at a high temperature of about 600 to 1100° C. by the reverse reaction of solid oxide fuel cells (SOFC) which will be described later. As shown in FIG. 5, the SOEC apparatus has a basic structure of an electrolyte made of solid oxide such as zirconium oxide modified by yttrium, and the electrolyte is sandwiched between a cathode and an anode respectively provided on both sides thereof. Water vapor supplied to the cathode side is decomposes into hydrogen and oxide ions, and the oxide ions pass through the electrolyte to become oxygen at the anode.

Figure 6:
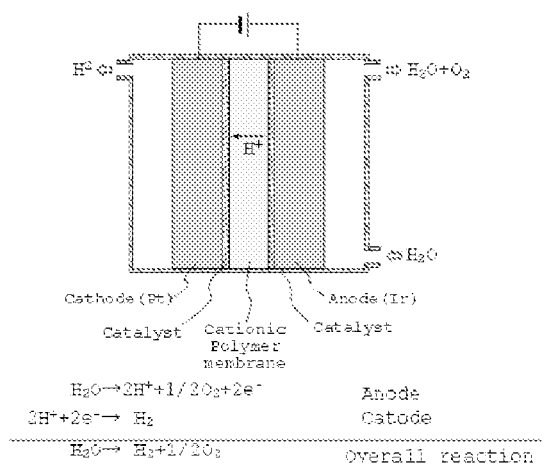
FIG. 6 shows a schematic longitudinal sectional view of a solid polymer water electrolyzer, which is another specific example of a hydrogen generator that constitutes the energy transportation system of the first embodiment of the present invention.
Figure 7:
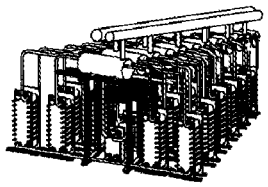
FIG. 7 shows a perspective view of a specific example of the solid polymer water electrolyzer of FIG. 6.

As shown in FIG. 6, the proton exchange membrane (PEM) water electrolyzer has a basic structure of a proton exchange membrane (PEM) made of a proton-conducting cationic polymer membrane as an electrolyte, and this electrolyte is provided with a cathode and an anode via catalyst layers on both sides thereof, respectively. The cathode is made of platinum-supported carbon, platinum-coated titanium, etc., and the anode is made of iridium oxide-coated titanium, iridium-ruthenium-nickel oxide, etc. It should be noted that the above-described PEM may mean a solid polymer membrane (Polymer Electrolyte Membrane) as well as a proton exchange membrane. Water ($H_2O$) supplied to the anode side is decomposed into oxygen and protons ($H^+$), and the protons pass through the proton exchange membrane and receive electrons at the cathode to become hydrogen. An example of a solid polymer water electrolyzer with the above structure is Silyzer 300 by SIEMENS' as shown in FIG. 7.

Figure 8:
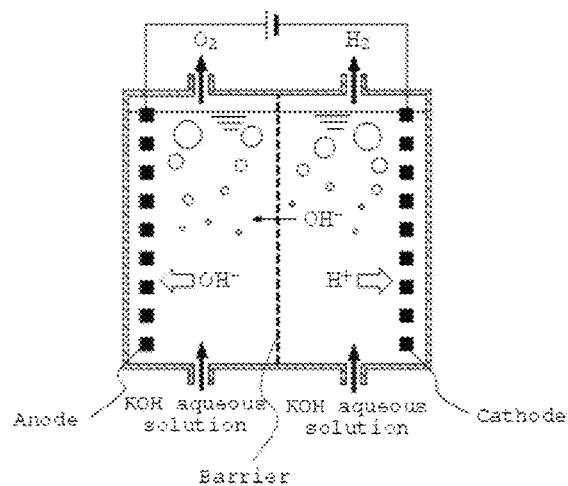
FIG. 8 shows a schematic longitudinal sectional view of an alkaline water electrolyzer, which is a further specific example of a hydrogen generator that constitutes the energy transportation system of the first embodiment of the present invention.

As shown in FIG. 8, the alkaline water electrolyzer has a basic structure of a partition wall as a gas barrier membrane, which is sandwiched between an anode and a cathode facing each other. The anode is made of lanthanum-doped cobalt oxide or nickel cobalt oxide etc., and the cathode is made of a high surface area catalytic electrode such as Raney nickel etc. Water molecules are decomposed into hydrogen ions and hydroxide ions at the cathode side, and these hydroxide ions pass through the partition wall to produce oxygen at the anode side. In any case of SOEC, PEM water electrolyzer, or alkaline water electrolyzer, it is preferable that the pressures of hydrogen and oxygen produced are in the range of 30 to 250 barA. If these pressures are less than 30 barA, the cost and power requirements of a compressor for pressurization will be excessive, while if these pressures exceed 250 barA, the oxygen content (impurities) in the hydrogen will increase too much. This pressure range can be achieved by stacking multiple cells in the water electrolyzer.

The hydrogen generator (water electrolyzer) M2 preferably has a hydrogen storage facility that stores a part of the hydrogen generated by the electrolysis of water, which can supply a fixed amount of hydrogen to the methane synthesizer M3 in the subsequent stage even if the amount of electricity generated by the power generator M1 fluctuates greatly due to wind conditions, which can vary day and night or seasonally. The specific structure of the hydrogen storage facility is not limited, and the facility may have a high-pressure hydrogen tank, which stores compressed hydrogen under high pressure, or the facility may use a hydrogen storage alloy made of alkaline earth alloy, rare earth alloy, titanium alloy, or other alloys. When storing hydrogen in the high-pressure hydrogen tank, it is preferable to use high-tensile steel such as API 5L-X80, special stainless steel, aluminum alloys, polymer composite materials, etc. as materials for the high-pressure hydrogen tank to prevent embrittlement due to high-pressure hydrogen.

Figure 9:
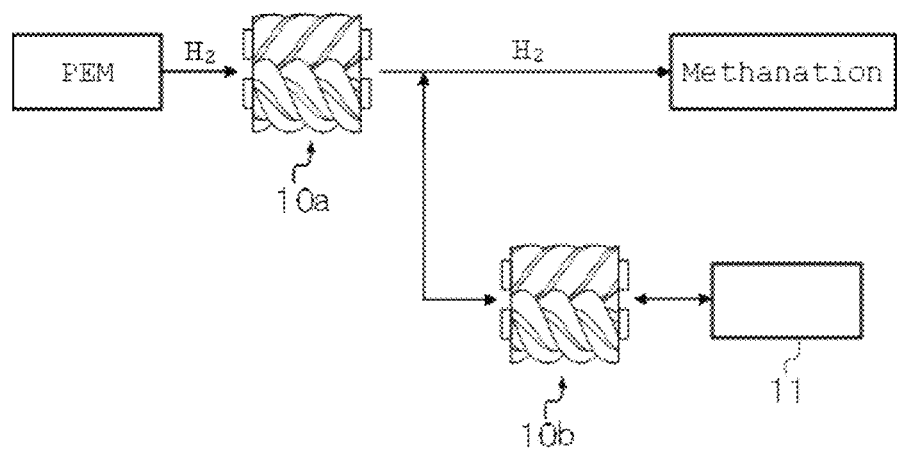
FIG. 9 shows a process flow diagram of a high-pressure hydrogen storage facility suitably having the water electrolyzer of FIG. 1.

FIG. 9 shows a process flow diagram of a high-pressure hydrogen storage facility where hydrogen produced by, for example, PEM as water electrolysis (hydrogen generator) M2 is stored in a high-pressure hydrogen tank. As shown in this process flow diagram of FIG. 9, the high-pressure hydrogen storage facility 11 is provided on a branch pipe that branches off from the piping that transfers hydrogen of, for example, about 1.0 to 5.0 MPaG, preferably 3.0 to 4.0 MPaG, more preferably 3.5 MPaG generated by a water electrolysis device of hydrogen generator M2 such as PEM to a methane synthesizer M3. FIG. 9 shows non-limiting configuration, in which hydrogen generated in the water electrolyzer M2 is supplied to the methane synthesizer M3 after being pressurized by the low-pressure screw compressor 10a, and the branch pipe is provided on the discharge side of the low-pressure screw compressor 10a.

Figure 10:
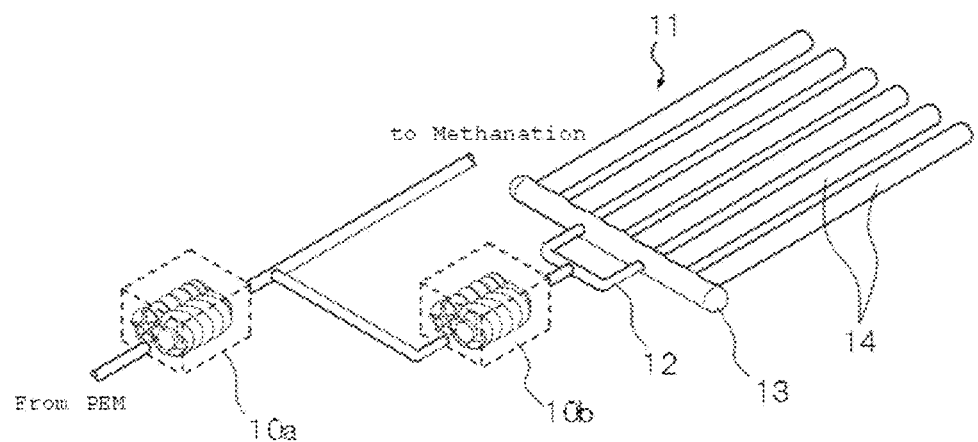
FIG. 10 shows a schematic view of a specific example of the high-pressure hydrogen storage facility shown in FIG. 9.

FIG. 10 shows a specific example of the high-pressure hydrogen storage facility described above. That is, the high-pressure hydrogen storage facility 11 shown in FIG. 10 mainly consists of a primary piping 12 that transports the high-pressure hydrogen which is generated by the water electrolyzer M2 using PEM or the like and is pressurized to, for example, about 10.0 to 45.0 MPaG, preferably 15.0 to 20.0 MPaG by using a low-pressure screw compressor 10a and a high-pressure screw compressor 10b, a manifold 13 that distributes the high-pressure hydrogen introduced via the primary piping 12, and a storage piping group 14 that includes a plurality of pipes that store the high-pressure hydrogen distributed by the manifold 13. When high-pressure hydrogen stored in the high-pressure hydrogen storage facility 11 is discharged, power can be recovered by using the high-pressure screw compressor 10b as a gas expander. In this case, adiabatic expansion of the gas lowers its temperature, while adiabatic compression conversely raises its temperature, and therefore heat exchangers may be respectively installed on the primary and secondary sides of the high-pressure screw compressor 10b for heat recovery/ heat disposal, if necessary.

The methane synthesizer M3, located in the subsequent stage of the hydrogen generator M2, produces methane by methanization of hydrogen (H₂) produced in the hydrogen generator M2 and recycled carbon dioxide (CO₂) as raw materials through the Sabatier reaction shown in Reaction Formula 1 below.

$$CO_2 + 4H_2 = CH_4 + 2H_2O \quad \text{[Reaction Formula 1]}$$

Figure 11A:
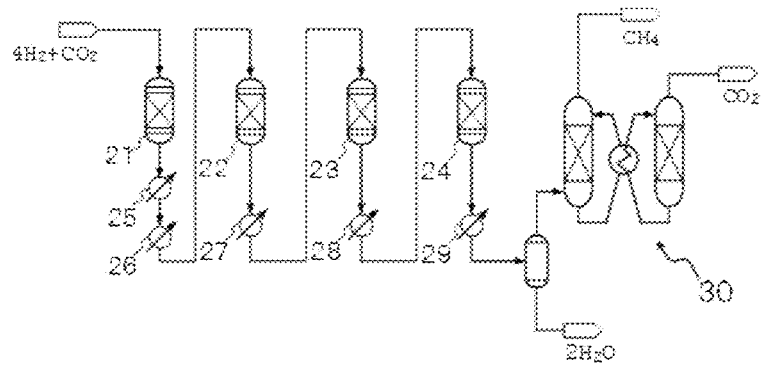
FIGS. 11A and 11B show a process flow diagrams of specific examples of methane synthesizers that constitute the energy transportation system of the first embodiment of the present invention.

The Sabatier reaction is carried out, for example, under a high temperature and high pressure of about 200 to 700° C. and 3.0 to 7.0 MPaG, in the presence of a catalyst of nickel series or ruthenium series loaded on a support in an amount of 5 to 20% by mass on the support basis, in which the support is made of alumina, magnesia, zirconia, yttrium oxide, ceria, titania, zeolite, or a solid solution containing two or more of these. Accordingly, a plurality of methane synthesis reactors 21 to 24 connected in series, as shown in FIG. 11A, are generally used for the methane synthesizer M3, so as to proceed the reaction step by step. Since the Sabatier reaction is an exothermic reaction, steam generators using water or coolers 25 to 29 using water as a refrigerant are installed at the subsequent stage of each of these methane synthesis reactors 21 to 24.

Figure 11B:
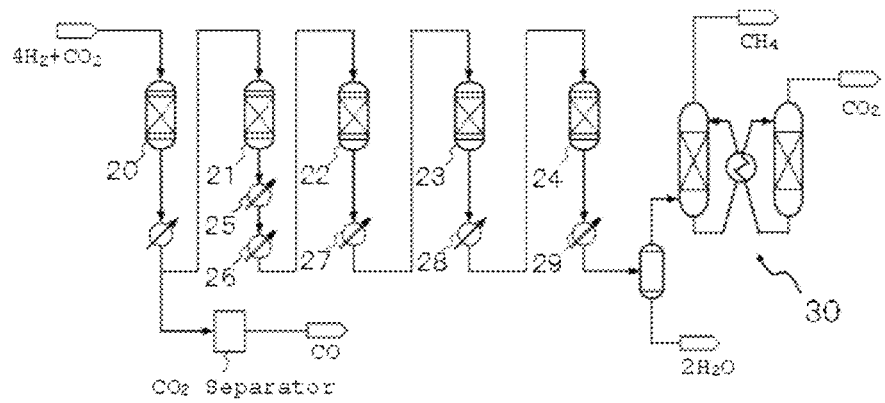

As shown in FIG. 11B, a reverse water gas shift reactor 20 which performs a reverse water gas shift reaction shown in Reaction Formula 2 below in the presence of a catalyst may be installed immediately before the reactors 21 to 24 that perform the above-described Sabatier reaction, in which the catalyst is, for example, Cu, Fe, Mo, K, etc. loaded on a support made of silica, alumina, etc. or a catalyst made of $BaZr_{0.5}Y_{0.2}O_3$, $BaCe_{0.2}Zr_{0.6}Y_{0.16}Zn_{0.04}O_3$, etc.

$$CO_2 + H_2 = CO + H_2O \quad \text{[Reaction Formula 2]}$$

The reverse water gas shift reaction can produce carbon monoxide (CO), which is more reactive than CO₂, and therefore oxo alcohols or higher hydrocarbons can be produced by the oxo alcohol synthesis reaction or Fischer-Tropsch reaction after extracting a part of the product gas and separating the CO therefrom. Since the Sabatier reaction is exothermic while the reverse water gas shift reaction is endothermic, the reaction heat generated in Sabatier reactors 21 to 24 can be used to heat the feed gas to the reverse water gas shift reactor 20 to increase the thermal efficiency of the entire system.

In the above-described Sabatier reaction, the stoichiometric amount of hydrogen is 4 moles to 1 mole of carbon dioxide gas, but it is not realistic in an actual system to achieve complete (100%) reaction with this stoichiometric amount, and about 2 to 4% of unreacted gas will remain in the product gas. Therefore, if the product gas of the Sabatier reaction is introduced directly into the methane liquefaction unit M4 in the subsequent stage, the carbon dioxide gas will solidify during the cooling process to form dry ice, which will lead to blockage of the liquefaction facility. It is therefore preferable to provide a carbon dioxide gas removal system 30 using amine solution or the like before the methane liquefaction unit M4 like a conventional LNG liquefaction plant. The carbon dioxide gas removed in the carbon dioxide gas removal system 30 can be recycled to the Sabatier reaction along with the hydrogen that is not liquefied in the liquefaction process described below.

Hydrogen, on the other hand, is not liquefied and is recycled to the methane synthesizer M3 as described below. In this instance, as shown in Table 2 below, it is preferable that an excess amount of hydrogen gas is introduced into the reactor in a range of 4.05 to 7.00 moles relative to a stoichiometric amount of 4 moles of hydrogen gas in the Sabatier reaction. This allows the Sabatier reaction to proceed in a direction of methane synthesis, which can reduce the number of the reactors. Since an increase in the amount of hydrogen gas recycled will increase the cost of the methane liquefaction facility, hydrogen recycling compressors, etc., the amount of hydrogen gas recycled is determined in consideration of the cost of methane synthesis.

TABLE 2

| mole ratio of H₂/CO₂ in methane synthesis feed | mole ratio of recycled CO₂/ synthesized methane | the number of reactors |
|---|---|---|
| 4.00 | 0.00 | 5 |
| 4.05 | 0.05 | 5 |
| 4.10 | 0.10 | 5 |
| 4.50 | 0.50 | 4 |
| 5.00 | 1.00 | 3 |
| 6.00 | 2.00 | 2 |
| 7.00 | 3.00 | 2 |

The methane liquefaction unit M4, which is located at subsequent stage of the methane synthesizer M3, can employ a liquefaction process that is in practical use in LNG plants that liquefies natural gas. Since the critical temperature of methane is −82° C., the liquefaction process employs a cryogenic liquefaction process such as the mixed refrigerant process, cascade process, and expander process, which can liquefy methane by cooling it to −162° C. under atmospheric pressure. In any of the above processes, the methane gas used as feed gas for the methane liquefaction unit M4 contains almost no impurities that can cause corrosion or other problems in the liquefaction facilities unlike the natural gas used as feedstock for LNG plants, and therefore a condensate separation facility and a mercury removal facility can be omitted.

Figure 12:
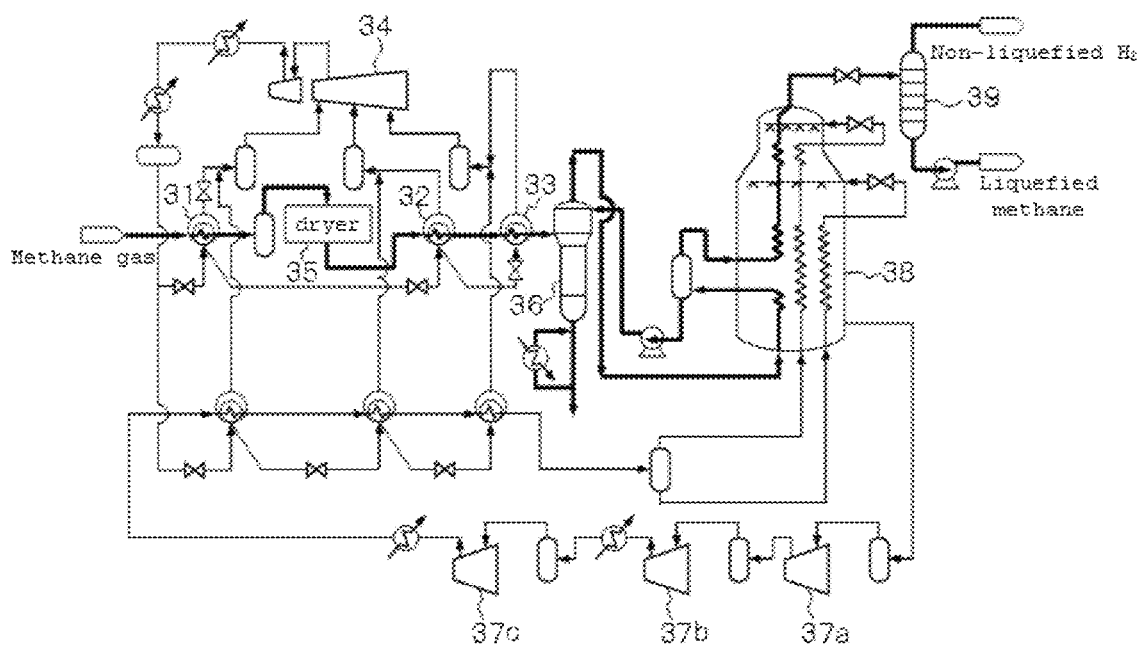
FIG. 12 shows a process flow diagram of a mixed refrigerant process, which is a specific example of a methane liquefaction unit that constitutes the energy transportation system of the first embodiment of the present invention.

The mixed refrigerant process is a method having a pre-cooling step using propane refrigerant followed by a cooling step using mixed refrigerant consisting of ethane, propane, etc. This process has been used in many projects under license from Air Products and Linde. Specifically, as shown in FIG. 12, in the mixed refrigerant process, the feedstock of methane gas is firstly introduced into a first kettle-type heat exchanger 31, a second kettle-type heat exchanger 32, and a third kettle-type heat exchanger 33 sequentially, such that the methane gas is pre-cooled in a stepwise manner with propane refrigerant which is compressed in three stages of low pressure stage, medium pressure stage, and high pressure stage by a propane multi-stage compressor 34. It should be noted that although FIG. 12 shows a scrubbing column 36 for hydrocarbon removal, which is required in natural gas liquefaction plants, the scrubbing column 36 can be omitted as mentioned above if the feedstock uses methane gas that is originated from methanation as in the first embodiment of the present invention. Further, if a process using non-aqueous solvent such as the SELEXOL process is used in the carbon dioxide removal facility 30 in a previous stage, a dryer 35 for dehydration can be omitted.

Figure 13:
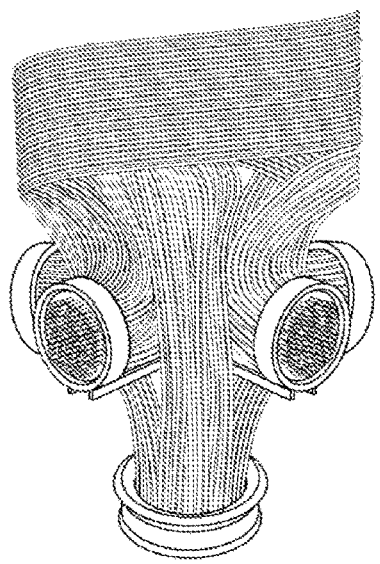
FIG. 13 shows a photograph showing a specific example of heat transfer tubes that constitutes the main cryogenic heat exchanger shown in the process flow diagram of FIG. 12.

Next, the methane pre-cooled with the above-described propane refrigerant is introduced into a main cryogenic heat exchanger 38 such that the methane gas is liquefied by cooling to about −140° C. by a mixed refrigerant sequentially compressed by MR compressors 37a to 37c, and then it is adiabatically expanded (isentropic expansion) by a flash drum 39 (also referred to a stripper), an expander, or Joule-Thomson expansion valve (J-T valve). The main cryogenic heat exchanger 38 has a structure like a Linde's main cryogenic heat exchanger as shown in FIG. 13, for example, in which an aluminum heat-transfer tube of about 10 mm in diameter is wound around a core rod in a coil shape and enclosed in a pressure vessel.

Figure 14:
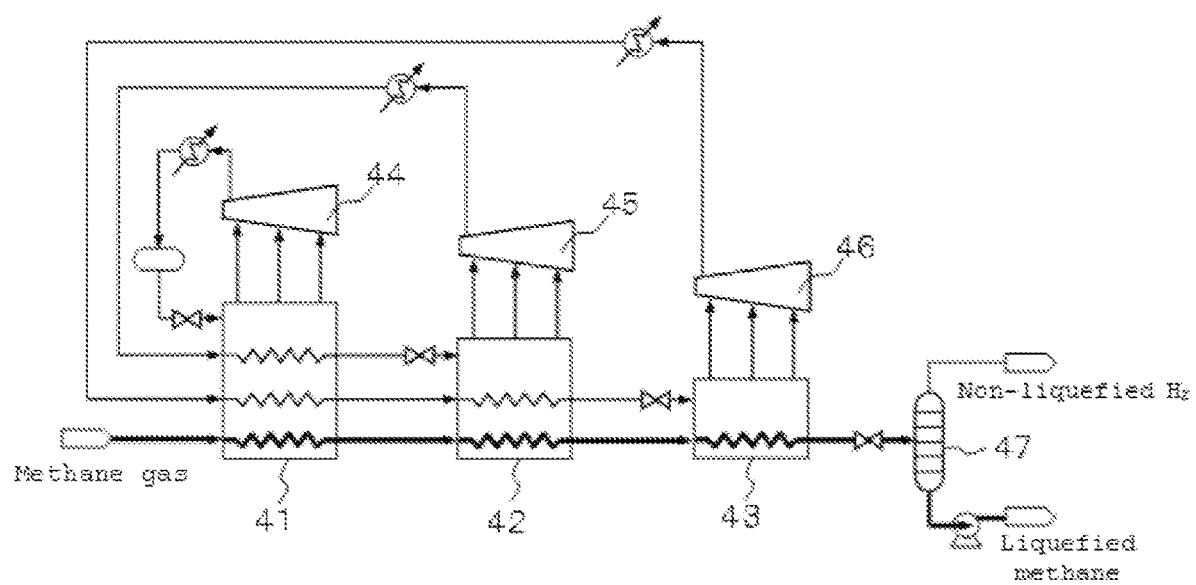
FIG. 14 shows a process flow diagram of a cascade process, which is another specific example of a methane liquefier that constitutes the energy transportation system of the first embodiment of the present invention.

In the cascade process, as shown in FIG. 14, the feedstock of methane gas is sequentially introduced into a first heat exchanger 41, a second heat exchanger 42, and a third heat exchanger 43, such that the methane gas is liquefied by sequential cooling through refrigeration cycles of single-component refrigerants with different temperature levels, consisting of a propane refrigerant system compressed by a propane compressor 44, an ethylene refrigerant system compressed by an ethylene compressor 45, and a methane refrigerant system compressed by a methane compressor 46, and then it is adiabatically expanded by a flash drum 47 in a similar manner as the mixed refrigerant process described above.

Figure 15:
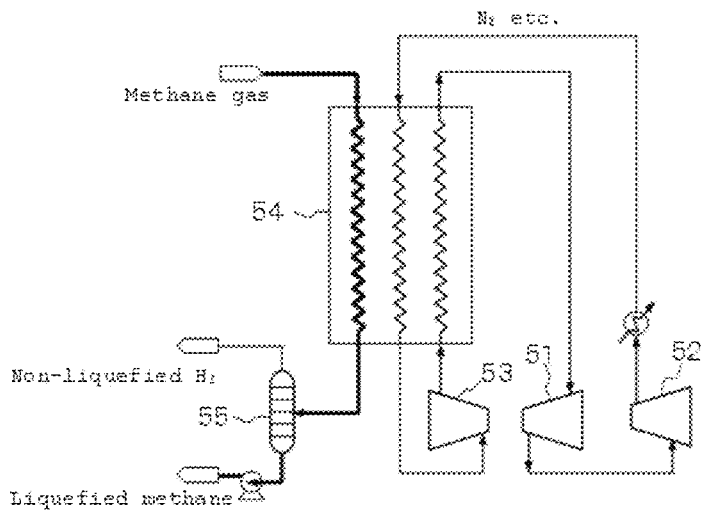
FIG. 15 shows a process flow diagram of an expander process, which is another specific example of a methane liquefier that constitutes the energy transportation system of the first embodiment of the present invention.

In the expander process, as shown in FIG. 15, nitrogen, methane, etc. are used as a refrigerant, and this refrigerant is circulated through a heat exchanger 54 while being compressed and expanded by, compressors 51, 52, and expander 53 respectively. The feedstock of methane gas is introduced into this heat exchanger 54 for liquefaction by cooling, and then it is adiabatically expanded by a flash drum 55 in a similar manner as the mixed refrigerant process described above.

Figure 16:
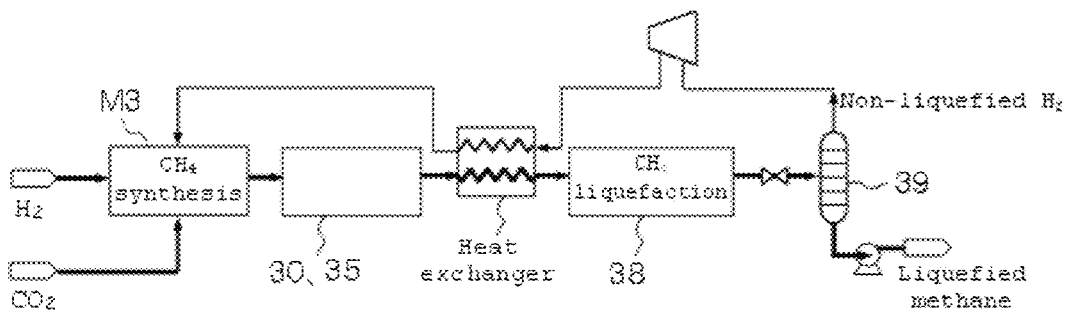
FIG. 16 shows a process flow diagram of a specific example of a process for recycling non-liquefied hydrogen generated in a methane liquefying unit, which constitutes the energy transportation system of the first embodiment of the present invention, to a methane synthesizer.

The flash drums 39, 47, and 55, which play the role of the stripper described above, all flash the liquefied methane liquefied by the methane gas liquefaction facility in the previous stage under a pressure of 0.8 to 2.0 barA and a temperature of −170 to −184° C. The non-liquefied hydrogen generated by the stripper is preferably recycled to the methane synthesizer M3 for reuse as a feedstock after recovering cold heat, for example, in the configuration shown in FIG. 16. It is preferable that the heat exchanger to exchange heat between methane and refrigerant in the methane liquefaction unit M4 is designed that the flow rate of methane, including the above-described non-liquefied hydrogen, is ensured to have at least 20% of the design flow rate. If this flow rate is less than 20% of the design flow rate, the pressure drop will be less than about 4% of the design flow rate, which may cause gas-liquid separation in the tubes or backflow of the liquid phase by gravity, and the performance of the heat exchanger may not be achieved. In the above heat exchanger, making a two-phase flow diagram can confirm whether the flow rate is ensured to have 20% or more of the design flow rate or not.

As described above, the lower limit of low-load operation of a coil-type heat exchanger using mixed refrigerant is generally about 20% of its design flow rate. Therefore, if it is desired to operate at a load lower than 20% of its design flow rate, it is preferable to adopt the above-described cascade process or expander process without using a coil-type heat exchanger, and the cascade process is more preferable. For example, in the case of the cascade process, the use of a shell-and-tube heat exchanger or a cross-flow plate-fin heat exchanger enables stable operation within the range of 1 to 100% of the design flow rate.

Figure 17:
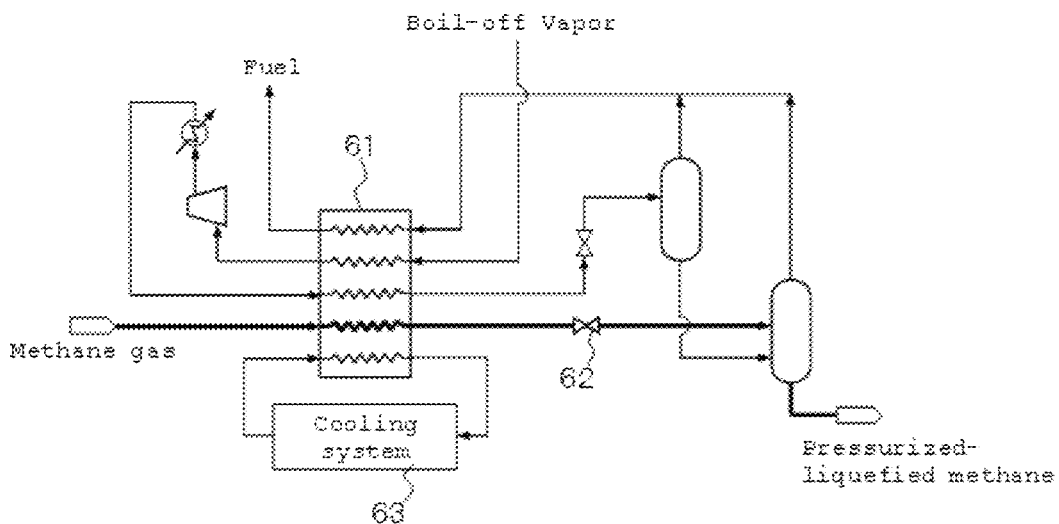
FIG. 17 shows a process flow diagram of a process for generating pressurized liquefied methane in a methane liquefier that constitutes the energy transportation system of the first embodiment of the present invention.

The above-described mixed refrigerant process, cascade process, and expander process all liquefies methane gas by cooling to about −160° C. under atmospheric pressure, but they can liquefy methane gas by cooling it to about −120 to −130° C. under pressurized condition. The pressurized liquefied methane can be produced, for example, by a liquefaction process shown in FIG. 17. In this liquefaction process shown in FIG. 17, a pre-pressurized methane gas is cooled by heat exchange with a refrigerant in a pressurized heat exchanger 61, such as a conventional plate fin heat exchanger or cold box heat exchanger, followed by flushing to partially depressurize to a pressure of 8.0 to 12.8 barA by using an expansion mechanism 62 such as an expansion valve, which thereby produces pressurized liquefied methane at a temperature of −120 to −130° C.

The refrigerant introduced into the pressurized heat exchanger 61 can be a single or multi-component substance suitable for refrigeration, such as propane, propylene, ethane, carbon dioxide, etc., and this refrigerant can be cooled by a cooling system 63 consisting of conventional heat exchanger and a refrigerant compressor. A boil-off gas generated from a storage tank, etc. of the pressurized liquefied methane and an exhaust gas discharged from a gas-liquid separation tank provided downstream of the expansion mechanism described above have approximately the same temperature as the pressurized liquefied methane, and therefore these gases can be used as a combustion gas after being heated up by recovery of cryogenic heat in the pressurized heat exchanger 61.

In the first embodiment of the present invention, it is preferable to use a rotary positive displacement type compressor driven by a synchronous motor for the refrigerant compressor in any of these liquefaction processes described above. The synchronous motor has a feature in that the motor rotates in synchronization with a frequency of an AC power source to be used, and by changing the AC frequency with an inverter, it is possible to freely control the number of rotations. A screw-type compressor is preferred for the rotary positive displacement type compressor. The reason for this is that when an output of the wind power generation fluctuates relatively moderate, i.e. from 70 to 100%, an axial flow type or a centrifugal type can be used, but when the fluctuation of this output is large, i.e. from 0 to 100%, use of the axial flow type or the centrifugal type necessitates a recycling operation to avoid surging that may occur in the 0 to 70% range, which wastes the drive power. In order to avoid this waste, it is preferable to use only the screw type, which is a rotary positive displacement type compressor, or to combine the screw type with the axial flow type or the centrifugal type.

Figure 18:
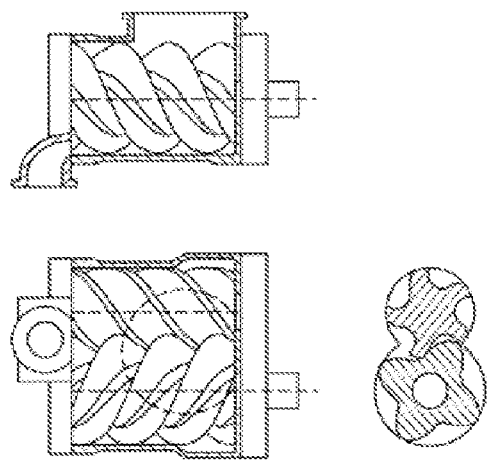
FIG. 18 shows a front, bottom, and cross-sectional views of a rotor portion of a specific example of a rotary displacement type refrigerant compressor suitably used in the methane liquefier that constitutes the energy transportation system of the first embodiment of the present invention.

The above-described screw type compressor has a structure in which a pair of rotors, each having spiral projections and spiral grooves that intermesh with each other, are enclosed in a casing as shown in FIG. 18, for example. A gas sucked in from an inlet of the casing is gradually pressurized by a decreasing space caused by meshing of the rotating pair of rotors, and then it is discharged from an outlet of the casing as a pressurized gas having a predetermined pressure.

Figure 19:
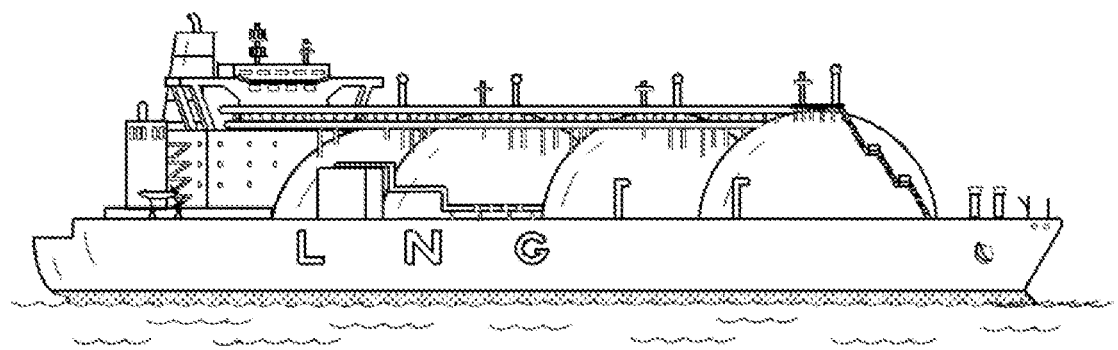
FIG. 19 shows a photograph of a specific example of an LNG tanker.
Figure 20:
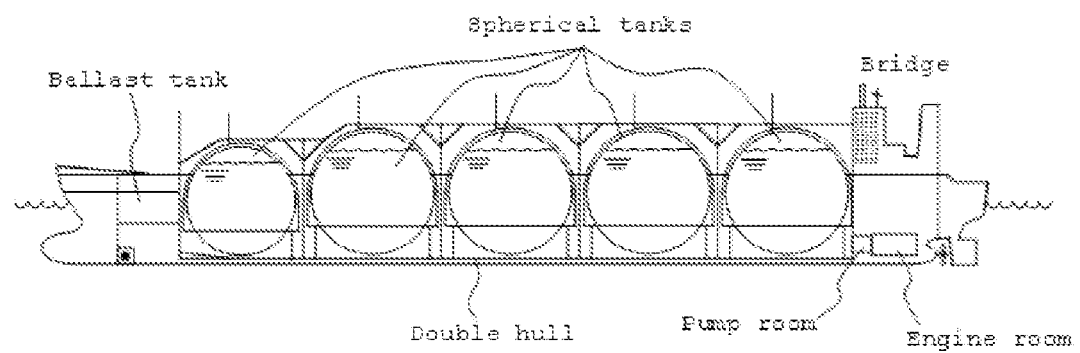
FIG. 20 shows a side view of a specific example of a cryogenic tanker suitably used in a liquefied methane transportation system and a liquefied $CO_2$ transportation system, which constitute the energy transportation system of the first embodiment of the present invention.

An LNG tanker used for marine transportation of LNG can be used for the liquefied methane transportation system M5 that transports a liquefied methane liquefied by the methane liquefaction unit M4 described above. When the LNG tanker is used, it is necessary to install a liquefied methane storage tank at a shipping terminal of the liquefied methane in order to load the liquefied methane to the LNG tanker. As shown in FIG. 19, an LNG tanker is equipped with a plurality of cryogenic tanks that store cryogenic LNG at approximately −162° C. at nearly atmospheric pressure. The LNG tanker is classified into several types including a Moss type structure that has a plurality of spherical independent tanks each mounted on a hull with cylindrical support members, a membrane type structure that has a heat insulator attached to an inside of the hull structure and a thin-film metal membrane attached to an inner surface of the heat insulator, and an SPB (Self-Supporting Prismatic-Shape IMO type B) type structure that has a plurality of independent square tanks attached to a hull via reinforced plywood supports. Among the above structures, the Moss type shown in FIG. 20 is preferred because of its abundant construction experience and economic efficiency.

The liquefied methane transportation system M5 is driven by a first power unit that does not emit $CO_2$ into the atmosphere. Such a first power unit can be either an engine-driven type by combustion of hydrogen or fossil fuel (internal combustion engine), which is accompanied by a facility to recover $CO_2$ in the exhaust gas emitted during the combustion in the case of fossil fuel combustion, or a battery-driven type. The former engine-driven type is classified into several types that includes a steam turbine type that combusts boil-off gas generated by a heat input from a tank, heavy oil, or both of these fossil fuels to generate steam in a boiler and the resulting steam is used to rotate a turbine, a second type that drives a generator by a diesel engine fueled by the above-described boil-off gas or heavy oil, and the resulting electricity is supplied to an electric motor to rotate a propeller, or a third type that directly drive the propeller by a gas-fired diesel engine that combusts a mixture of these boil-off gas and heavy oil. In all of these types, a $CO_2$ recovery facility is required because combustion exhaust gas containing $CO_2$ is discharged during the combustion of fossil fuels. There is no particular limitation regarding the type of $CO_2$ recovery facility, and for example, a method of absorption by a chemical absorption solution in a similar manner to a $CO_2$ recovery facility provided in conjunction with a CCGT power generation as described below can be suitably adopted. The $CO_2$ recovered from the flue gas containing $CO_2$ can be reused as a raw material in the methane synthesizer M3.

On the other hand, a secondary battery that can be repeatedly charged and discharged is used for the latter battery-driven type, and in particular, it is preferable to use a lithium-ion secondary (rechargeable) battery in which charging and discharging is repeated by lithium ions moving between the positive electrode and negative electrode facing each other with a separator between them. The lithium-ion secondary battery can be charged using either electricity from the above-described renewable energy from the power generator M1 or electricity from the power generation and carbon capture unit M7, both of which can propel a cryogenic tanker without generating $CO_2$.

Figure 21:
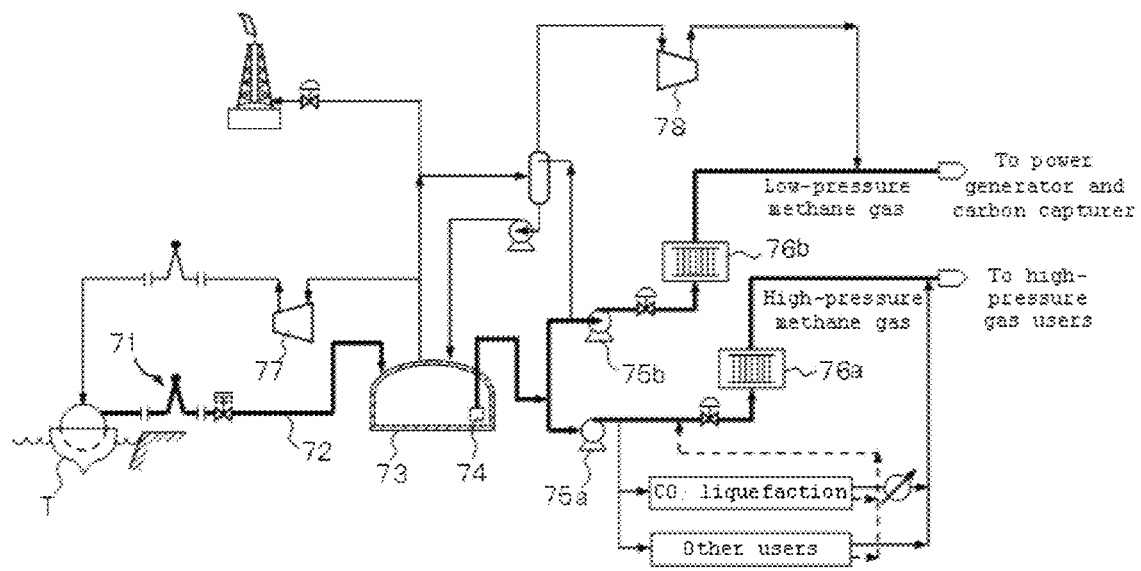
FIG. 21 shows a process flow diagram of a specific example of a liquefied methane receiving and regasifying unit that constitutes the energy transportation system of the first embodiment of the present invention.

The liquefied methane transported by the liquefied methane transportation system M5 is received by the liquefied methane receiving and regasifying unit M6. As shown in FIG. 21, the liquefied methane receiving and regasifying unit M6 mainly consists of a liquefied methane tank 73 that stores liquefied methane at the liquefied methane receiving terminal, and vaporizers 76a and 76b that regasify liquefied methane, which is discharged from the liquefied methane tank 73 by the first pump 74, using a heat medium such as sea water. A high-pressure methane gas and a low-pressure methane gas are produced by regasification in vaporizers 76a and 76b, of which the low-pressure methane gas is sent to the power generation and carbon capture unit M7 in the subsequent stage, where it is combusted for power generation.

Specifically, the liquefied methane unloaded from the cryogenic tanker T is received into the liquefied methane tank 73 via the unloading arm 71 and the unloading line 72. The structure of liquefied methane tank 73 is not limited, and its type can be, for example, a ground metal two-shell high-floor type that consists of an inner tank made of 9% Ni steel or aluminum alloy and an outer tank made of common carbon steel, with perlite filled and nitrogen introduced between the inner and outer tanks, a PC outer tank type that uses a pre-stressed concrete (PC) instead of carbon steel for the outer tank of the ground metal two-shell high-floor type, or an underground membrane type that has a cold insulator inside a concrete frame and a stainless steel membrane is stretched over an inner surface of the cold insulator.

The liquefied methane discharged from the above-described liquefied methane tank 73 by the first pump 74 is pressurized by the second pump 75a for high pressure service or the booster pump 75b for low pressure service, and then respectively introduced into the vaporizer 76a for high pressure service or the vaporizer 76b for low pressure service. A part of a boil-off gas generated by the heat input to the liquefied methane tank 73 is pressurized by the return gas blower 77 and introduced into the low-temperature tank of the cryogenic tanker T in order to suppress the pressure drop in the tank of the cryogenic tanker T during unloading of the liquefied methane. The remaining boil-off gas is pressurized to a predetermined pressure by the BOG compressor 78 and then sent to the power generation and carbon capture unit M7 together with the low-temperature methane gas vaporized in the above-described vaporizer 76b. The liquefied methane pressurized by the second pump 75a is partially extracted and used as a refrigerant for the $CO_2$ liquefaction system described below.

Figure 22:
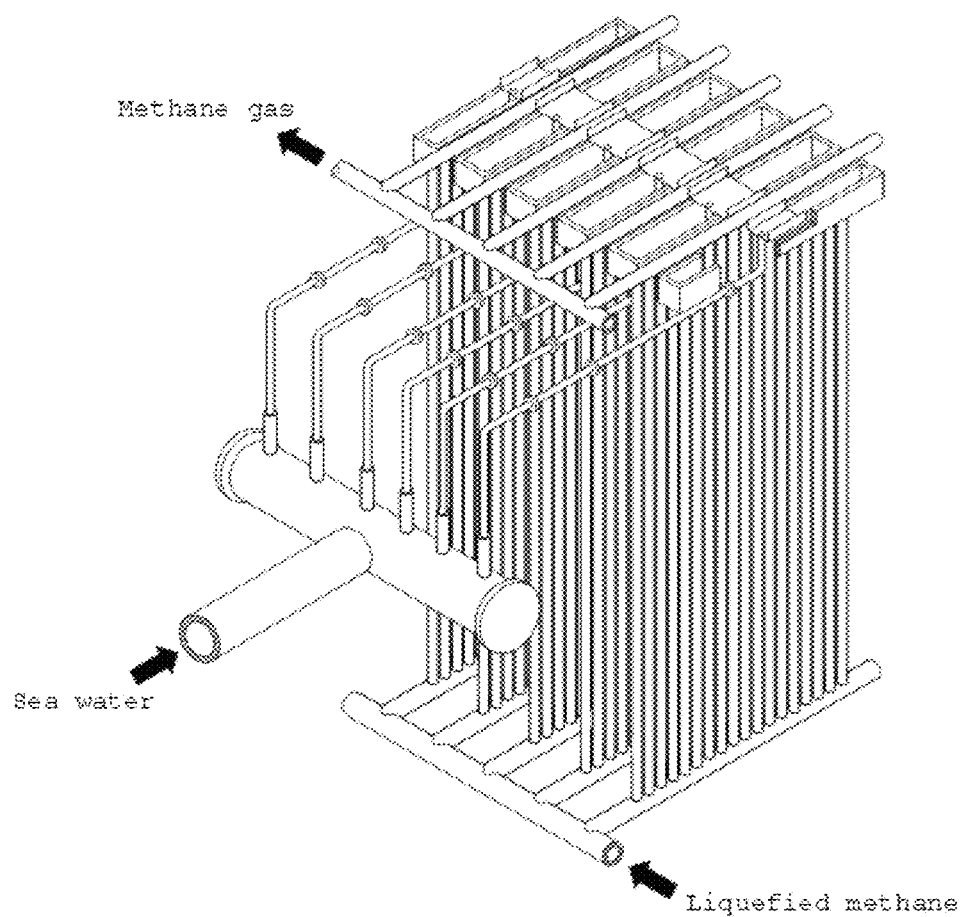
FIG. 22 shows a partially cutout perspective view of a specific example of a vaporizer shown in the process flow diagram of FIG. 21.

LNG vaporizers can be used for the above-described vaporizers, and either one of the following types is adopted that is an open rack type in which the liquefied methane is vaporized by exchanging heat with seawater flowing down the surface of the panels, a submerged type in which heat exchange tubes are provided in a concrete water tank, such that LNG introduced into the heat exchanger tubes is vaporizes by water to which a high-temperature combustion gas generated by a combustion burner is injected for heating, an intermediate heat medium type in which LNG introduced into one side of a shell-and-tube heat exchanger is vaporized by an intermediate medium such as propane evaporated in seawater and introduced into the other side of the heat exchanger, or an air temperature type in which air is used as the heat source. Although any of these types can be adopted, the open rack type shown in FIG. 22 is more preferable because it is inexpensive to operate and has many achievements. Alternatively, compressed $CO_2$ can be used as a heat source.

In the power generation and carbon capture unit M7, the above-described methane gas regasified in the liquefied methane receiving and regasifying unit M6 is subject to react with oxygen to generate electricity. In this case, one of the following power generation methods can be used: combined cycle power generation, power generation using solid oxide fuel cells, or power generation using the Allam cycle with an oxygen plant and a carbon dioxide cycle.

Figure 23:
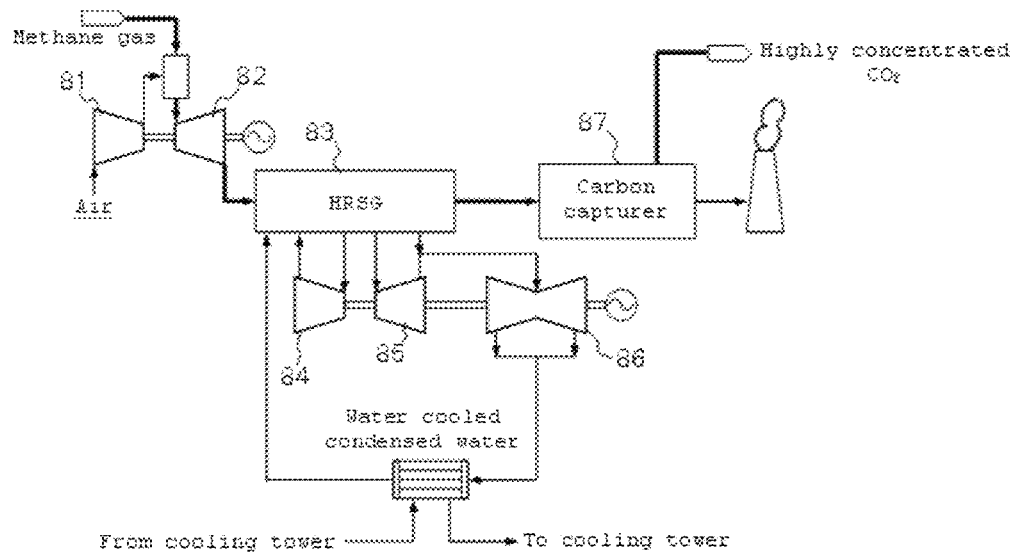
FIG. 23 shows a process flow diagram of a combined cycle power generator, which is a specific example of a power generation and carbon capture unit that constitutes the energy transportation system of the first embodiment of the present invention.

Combined cycle power generation (also referred to as GTCC) is a two-type power generation system that combines a gas turbine and a steam turbine, as shown in FIG. 23, and can improve power generation efficiency by about 20% as compared with conventional coal-fired thermal power generation. Specifically, methane gas is first combusted in air compressed by the compressor 81 to generate high-temperature and high-pressure combustion gas, which is used to rotate the gas turbine 82, which has a common rotating shaft with the compressor 81, to generate electricity. The combustion gas used to rotate the gas turbine 82 still has a high enough temperature, and thus it is introduced into the waste heat recovery boiler (HRSG) 83, where the residual heat is used to evaporate water to generate three types of steam at different pressure levels: high pressure (HP), medium pressure (IP), and low pressure (LP). The HP turbine 84, IP turbine 85, and LP turbine 86 are respectively rotated by these pressures to generate electricity.

An exhaust gas discharged from the waste heat recovery boiler 85 contains $CO_2$ produced by the combustion of the above-described methane gas, which is separated and recovered in the carbon recovery unit (carbon capturer) 87. There are no particular limitations regarding the method of $CO_2$ separation and recovery in the carbon recovery unit 87, and the method can be a chemical absorption method in which $CO_2$ is chemically absorbed using a solvent such as amine, a physical absorption method in which $CO_2$ is absorbed by a physical absorption solution such as methanol under high pressure, a membrane separation method in which $CO_2$ is separated using a membrane through which $CO_2$ is selectively permeated, or a physical adsorption method in which $CO_2$ is adsorbed onto a solid adsorbent such as molecular sieve (synthetic zeolite) and then $CO_2$ is desorbed and recovered by depressurizing or heating the adsorbent.

Figure 24:
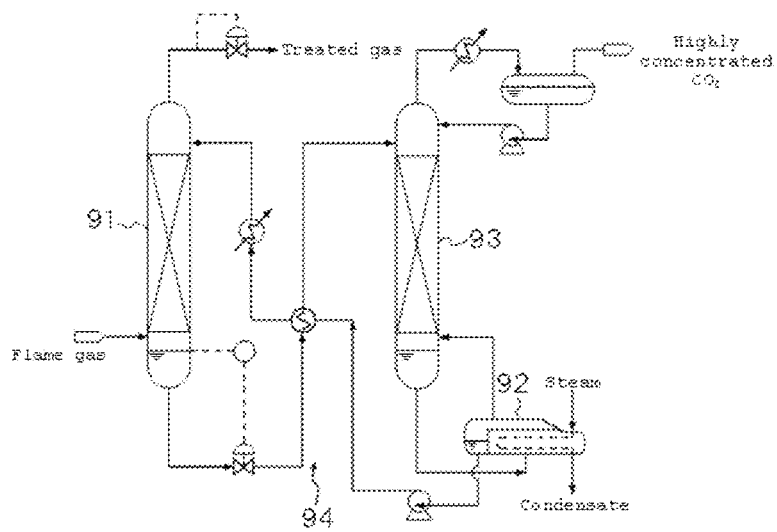
FIG. 24 shows a process flow diagram of an amine absorbent process, which is a specific example of the carbon capture unit shown in the process flow diagram of FIG. 23.

Among these methods, the chemical absorption method or physical adsorption method is preferred, and the chemical absorption method using amine absorption liquid or the physical adsorption method using molecular sieve is more preferred, and the chemical absorption method using amine absorption liquid is most preferred. The facility to perform the chemical absorption method using amine absorption liquid is shown in FIG. 24, for example, which includes an absorption column 91 in which gas-liquid contact is performed between the flue gas containing $CO_2$ and an amine absorption liquid, a reboiler 92 in which the rich amine absorption liquid containing $CO_2$ absorbed in the absorption column 91 in the form of amine carbonate is heated to about 110 to 130° C., a regeneration column 93 in which $CO_2$ is dissociated from the rich amine so as to recover the $CO_2$ from the top of the column as highly concentrated $CO_2$ gas with a $CO_2$ concentration of 99 vol % (dry basis) or higher, and to regenerate the rich amine absorption liquid as lean amine absorption liquid, and a circulation system 94 that circulates the amine absorption liquid between the absorption column 91 and the regeneration column 93.

Fuel cells use a technology that generates electricity through a chemical reaction between hydrogen and oxygen, which is the reverse reaction of the electrolysis of water. Typical fuel cells are categorized into four (4) types; a solid oxide fuel cell (SOFC) that uses an oxygen ion conductive solid oxide as an electrolyte, a phosphoric-acid fuel cell (PAFC) that uses a hydrogen conductive aqueous solution of phosphoric acid as an electrolyte, a molten carbonate fuel cell (MCFC) that use a mixture of carbonate ion conductive lithium carbonate and sodium carbonate as an electrolyte, and a solid polymer electrolyte fuel cell (PEFC) that use a hydrogen ion conductive solid polymer membrane as the electrolyte. In the power generation and carbon capture unit M7 of the first embodiment of the present invention, any of the above types of fuel cells can be employed by providing a reformer to generate hydrogen from methane gas in a previous stage, but the solid oxide fuel cell (SOFC), which have the highest power generation efficiency among these, is more preferred.

Figure 25:
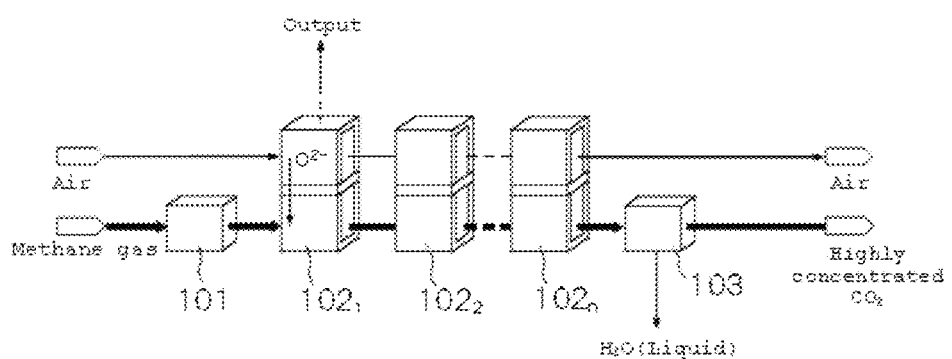
FIG. 25 shows a process flow diagram of power generation by a solid oxide fuel cell, which is another specific example of the power generation and carbon capture unit that constitutes the energy transportation system of the first embodiment of the present invention.

The solid oxide fuel cell consists of the equipment shown in FIG. 25, for example. Namely, the equipment shown in FIG. 25 consists of a reformer 101 that generates hydrogen and carbon monoxide by a reforming reaction of methane gas and water under a catalyst, a multi-stage flat plate fuel cell $102_1$, $102_2$, $-102_n$ in which n-stage flat-plate single cells are connected in series where each of the cells having a structure of an air pole and a fuel pole facing each other in a vertical direction with a ceramic electrolyte made of, for example, zirconia etc. being sandwiched therebetween, and a device 103 that cools the exhaust gas discharged from the fuel electrode side of the final stage fuel cell $102_n$ to separate and remove condensate, and further concentrates $CO_2$ using an amine device or the like to recover highly concentrated $CO_2$ gas with a $CO_2$ concentration of 98% or more by volume.

Figure 26:
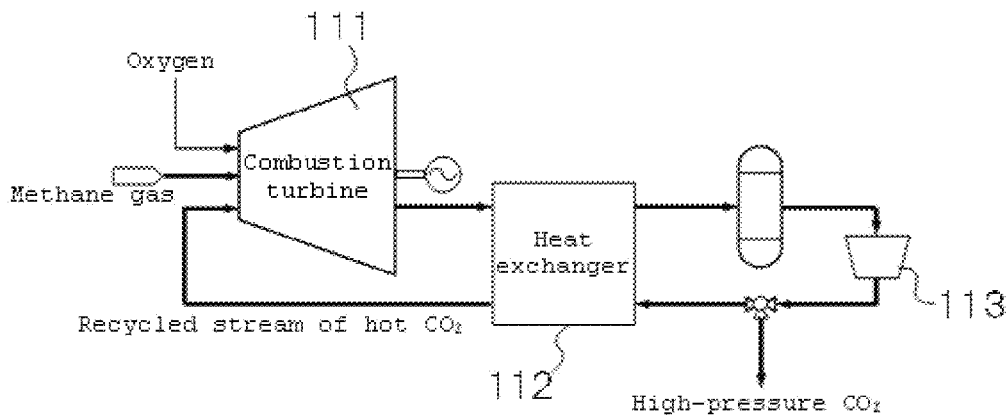
FIG. 26 shows a process flow diagram of power generation by an Allam cycle, which is another specific example of a power generation and carbon capture unit that constitutes the energy transportation system of the first embodiment of the present invention.

The Allam cycle is a supercritical $CO_2$ cycle power generation system. As shown in FIG. 26, the Allam cycle is performed by a system that combusts the methane gas as a fuel with oxygen in a $CO_2$ atmosphere, and a high temperature and high pressure mixture gas of $CO_2$ and steam generated by this combustion is used to rotate the turbine 111 to generate electricity. An exhaust gas discharged from the turbine 111 is cooled in the heat exchanger 112 to separate and remove steam as condensate, and then compressed in the compressor 113 to recover $CO_2$ as a highly concentrated $CO_2$ gas containing more than 98% volume of $CO_2$ produced from carbon derived from methane gas.

Figure 27:
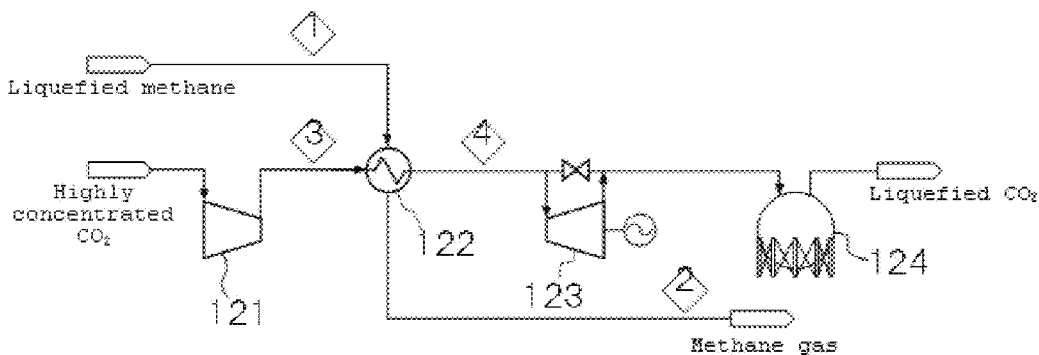
FIG. 27 shows a process flow diagram of a specific example of a $CO_2$ liquefaction unit that constitutes the energy transportation system of the first embodiment of the present invention, and its material and heat balances.

The recycled $CO_2$ recovered in the power generation and carbon capture unit M7 is transferred to the $CO_2$ liquefaction unit. As shown in FIG. 27, the $CO_2$ liquefaction unit includes the compressor 121 that compresses the recycled $CO_2$ to a pressure of 45 to 80 barA, the heat exchanger 122 that liquefies the recycled $CO_2$ by cooling down to a temperature of −33 to −56° C. by using a cryogenic heat that is generated when regasifies the liquefied methane compressed by the second pump 75a of the receiving and regasifying unit M6 to a pressure of 10 to 100 barA, and a liquid turbine 123 to recover power by depressurizing the liquefied $CO_2$ liquefied by the heat exchanger 122 to a pressure of 5.2 to 12.8 barA. FIG. 27 shows the results of the heat balance calculation when liquefying the recycled $CO_2$ of 65 barA with liquefied methane of 50 barA.

Liquid $CO_2$ at a temperature of −56 to −33° C., which has been depressurized to a pressure of 5.2 to 12.8 barA by the above-described liquid turbine 123, is stored in the insulated spherical storage tank 124 that can store the liquefied $CO_2$ under these pressure and temperature conditions. The liquefied $CO_2$ stored in this spherical storage tank 124 is loaded onto a liquefied $CO_2$ tanker as a $CO_2$ transportation system and transported to a methane synthesis site, where the liquefied $CO_2$ is regasified and then used in the methane synthesizer M3 as a feedstock for the Sabatier reaction. There is no particular limitation regarding the regasification method of this liquid $CO_2$. For example, it is preferable that seawater or fresh water is used to heat the liquid $CO_2$ having a temperature of −56 to −33° C. to about 0° C., and waste heat from the product gas of the Sabatier reaction is used to heat it from 0° C. to about 200° C.

Figure 28:
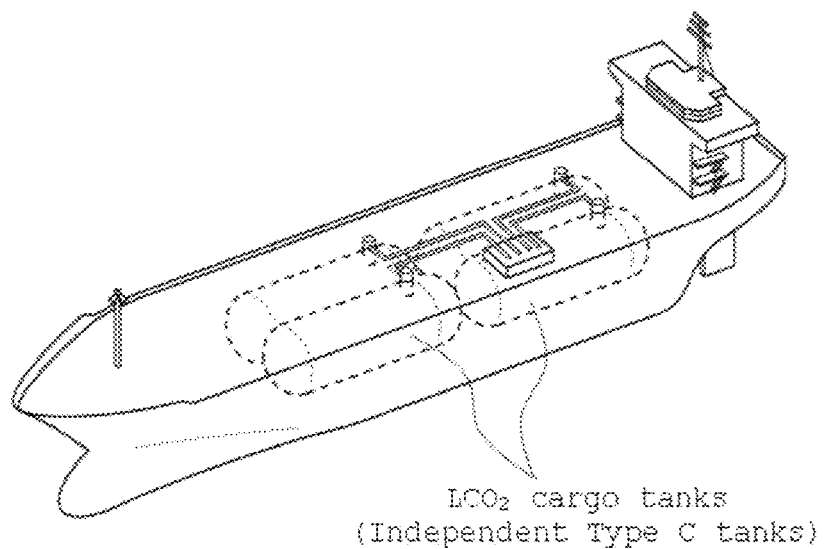
FIG. 28 shows a perspective view of a specific example of a cryogenic tanker for liquefied $CO_2$ equipped with a plurality of horizontal cylindrical tanks.

As mentioned above, the temperature and pressure of the liquefied methane and the liquefied $CO_2$ are both different, so it is preferable to use dedicated cryogenic tankers for transporting these liquefied methane and liquefied $CO_2$, respectively. During this tanker transportation, the liquefied $CO_2$ in tankers reaches pressures of 5.2 to 12.8 barA and temperatures of −56 to −33° C., it is therefore preferable that tank material of cryogenic tankers for liquefied $CO_2$ is low-temperature service steel such as aluminum-killed carbon steel, 1.5% Ni nickel steel, or high-tensile strength nickel steel for low-temperature service. Since liquefied $CO_2$ has a higher liquid density than liquefied methane, it is preferable to use a cryogenic tanker for liquefied $CO_2$ with, for example, four (4) to eight (8) cylindrical tanks that are turned sideways (horizontal shape) as shown in FIG. 28 in order to keep the center of gravity of the tanker low.

On the other hand, for cryogenic tankers for liquefied methane, it is preferable to use Moss-type tankers with 3 to 7 spherical tanks, and materials of these spherical tanks should include the following: if the liquefied methane during transportation reaches pressures of −0.05 to 0.25 barG and a temperature of −162° C., preferred materials for these spherical tanks are 6-7.5% Ni steel (JIS, SL7N590), 8.5-9.5% Ni steel (JIS, SL9N590), 18-8 stainless steel, or aluminum alloy 5083, or if the liquefied methane reaches pressures of 8.0-12.8 barA and temperatures of −120 to −130° C., 6-7.5% Ni steel, 8.5-9.5% Ni steel, 18-8 stainless steel, aluminum alloy 5083, or 5% Ni steel is preferred.

If a common cryogenic tanker can be shared for transporting the liquefied methane and the liquefied $CO_2$, instead of using dedicated cryogenic tankers as described above, a significant cost reduction can be achieved because a dedicated tanker for liquefied $CO_2$ will not be needed. In other words, if a cryogenic tanker that loads liquefied methane at the liquefied methane shipping terminal at the PtG complex and transports the liquefied methane to the liquefied methane receiving terminal at the power generation complex can be shared with a cryogenic tanker that loads liquefied $CO_2$ at the liquefied $CO_2$ shipping terminal at the power generation complex and transports the liquefied $CO_2$ from there to the PtG complex for the return journey, transportation costs can be significantly reduced. In this case, the cryogenic tanker with 3 to 7 spherical tanks, or 4 to 8 horizontal cylindrical tanks can also be used, as described above. However, since liquefied methane needs to be transported at lower temperatures than liquefied $CO_2$, the material of these spherical tanks or horizontal cylindrical tanks must be selected to withstand such low-temperature liquefied methane.

Specifically, when a transporting condition of liquefied methane is at a pressure of −0.05 to 0.25 barG and a temperature of −162° C., and a transporting condition of liquefied $CO_2$ is at a pressure of 5.2 to 12.8 barA and a temperature of −56° C. to −33° C., the tank materials of the common cryogenic tanker used for transporting the liquefied methane and the liquefied $CO_2$ should be selected from among 6-7.5% Ni steel, 8.5-9.5% Ni steel, 18-8 stainless steel, and aluminum alloy 5083.

On the other hand, when a transporting condition of pressurized liquefied methane is at a pressure of 8.0 to 12.8 barG and a temperature of −120 to −130° C., and a transporting condition of liquefied $CO_2$ is at a pressure of 5.2 to 10.8 barA and a temperature of −56° C. to −33° C., the tank materials of the common cryogenic tanker used for transporting the pressurized liquefied methane and the liquefied $CO_2$ should be selected from among 6-7.5% Ni steel, 8.5-9.5% Ni steel, 18-8 stainless steel, aluminum alloy 5083, and 5% Ni steel. Transporting the liquefied methane in the pressurized condition would allow the use of 5% Ni steel, which is less expensive than 6-7.5% Ni steel, 8.5-9.5% Ni steel, 18-8 stainless steel, and aluminum alloy 5083.

1-2 Green Energy Transportation Method

Next, an energy transportation method using the green energy transportation system of the first embodiment of the present invention described above will be described. The energy transportation method using the energy transportation system of the first embodiment of the present invention includes a power generation step that generates and stores electricity from a renewable energy, a hydrogen generation step that generates hydrogen by electrolysis of water using electricity obtained in the power generation step, a methane synthesis step that generates methane by methanation through a Sabatier reaction using the hydrogen produced in the hydrogen generation step and a recycled $CO_2$ as raw materials, a methane liquefaction step that liquefies methane by using a rotary positive displacement type refrigerant compressor driven by a synchronous motor to which electricity from the renewable energy is supplied as an energy source via a variable speed motor inverter so as to transport the methane produced in the methane synthesis step in the form of liquefied methane, a methane transportation step that transports the methane produced in the methane synthesis step and liquefied in the methane liquefaction step to an energy consumption site without emitting $CO_2$ into the atmosphere, a liquefied methane receiving and regasifying step that regasifies the liquefied methane after received it into a liquid methane storage tank, a power generation and carbon capture step that generates electricity by using the methane, which is transported in the form of liquefied methane by the methane transportation step and then temporarily received and regasified in the liquefied methane receiving and regasifying step, as a feedstock to react with oxygen, and recovers carbon discharged during the generation of electricity in a form of recycled $CO_2$ consisting of highly concentrated $CO_2$ gas, and a $CO_2$ transportation step that transports the recycled $CO_2$ recovered in the power generation and carbon capture step to a site where the methane synthesis step is performed without emitting $CO_2$ into the atmosphere.

The methane transportation step transports liquefied methane liquefied in the methane liquefaction step to the energy consumption site by a liquefied methane tanker driven by the first power unit without $CO_2$ emissions to the atmosphere. The power generation and carbon capture step has a $CO_2$ liquefaction step that liquefies the recycled $CO_2$ so as to transport the recovered recycled $CO_2$ in the form of liquid $CO_2$, and the methane synthesis step has a liquefied $CO_2$ receiving and regasifying step that regasifies the liquefied $CO_2$ transported in the liquefied $CO_2$ transport step after receiving it into the liquefied $CO_2$ storage tank. In this case, the $CO_2$ transportation step transports the liquefied $CO_2$ liquefied in the $CO_2$ liquefaction step to the methane synthesis site where the methane synthesis step is performed by a liquefied $CO_2$ tanker driven by a second power unit without $CO_2$ emissions to the atmosphere. The second power unit that does not emit $CO_2$ into the atmosphere uses, as in the case of the liquefied methane transportation system M5 described above, an engine driven unit by combustion of hydrogen or fossil fuel (internal combustion engine), and in the case of fossil fuel combustion, it is accompanied by a facility to recover $CO_2$ in the exhaust gas discharged during the combustion, or battery-driven unit such as a lithium-ion rechargeable battery.

Figure 29:
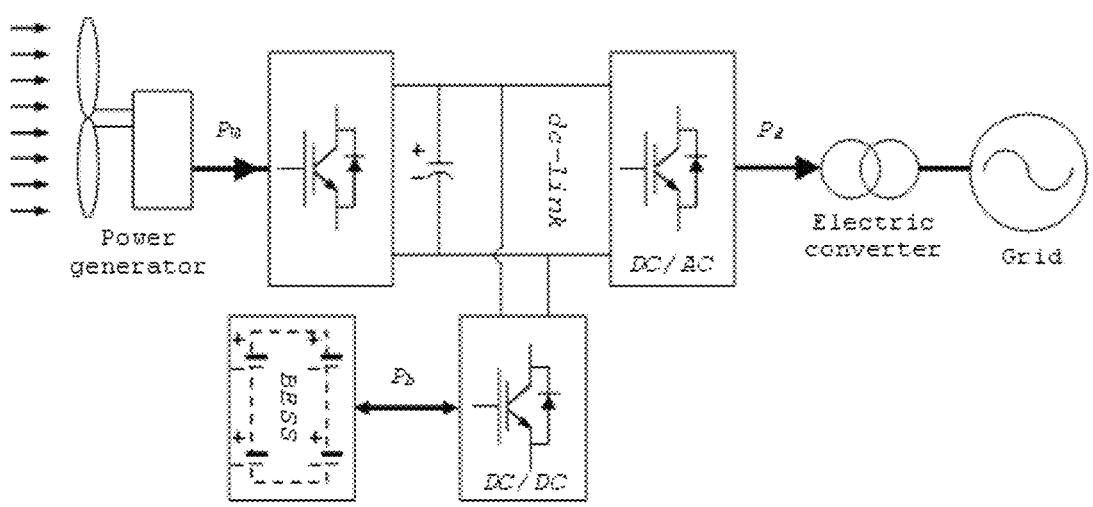
FIG. 29 shows a diagram of a specific example of a wind turbine generator using a permanent magnet synchronous generator and storage batteries included in a power generator that constitute the energy transportation system of the first embodiment of the present invention.

In the power generation step for generating electricity from renewable energy sources described above, any of the following renewable energy sources may be used as energy sources: wind power, photovoltaic power, solar thermal power, geothermal power, hydroelectric power, biomass power, wave/tidal-current/tidal power, etc., but wind turbine generators are suitably employed. In this case, a storage battery installed beside the above-described wind turbine generator should be set to have a capacity value in the range of 106 to 126% of the wind turbine rating of the wind turbine generator, and the storage battery should be operated in the operational range of 20 to 90% of the wind turbine rating. FIG. 29 shows a configuration diagram of a specific example of a wind turbine generator using a permanent magnet synchronous generator and a storage battery.

In the electrolysis of water in the above-described hydrogen generation step, the minimum electrolysis load, which is the power required for the electrolysis of water, should be preferably set within the range of 5 to 30% of the wind turbine rating. It is preferable to control the system such that if the power generated by the wind turbine generator, whose variable is the wind speed, is less than the minimum electrolysis load, its shortage is made up from the storage battery in which the above storage is performed. Whereas if the power generated by the wind turbine is equal to or above the minimum electrolysis load, the generated power is used for the electrolysis of water, and an excess power of the generated power over the minimum electrolysis load is charged to the storage battery under conditions of below an upper limit set within a range of 5 to 15% of the wind turbine rating and within the operational range of the storage battery. In principle, this control scheme allows the methane liquefaction processing of the methane liquefaction facility to be operated successively without stopping.

Figure 30:
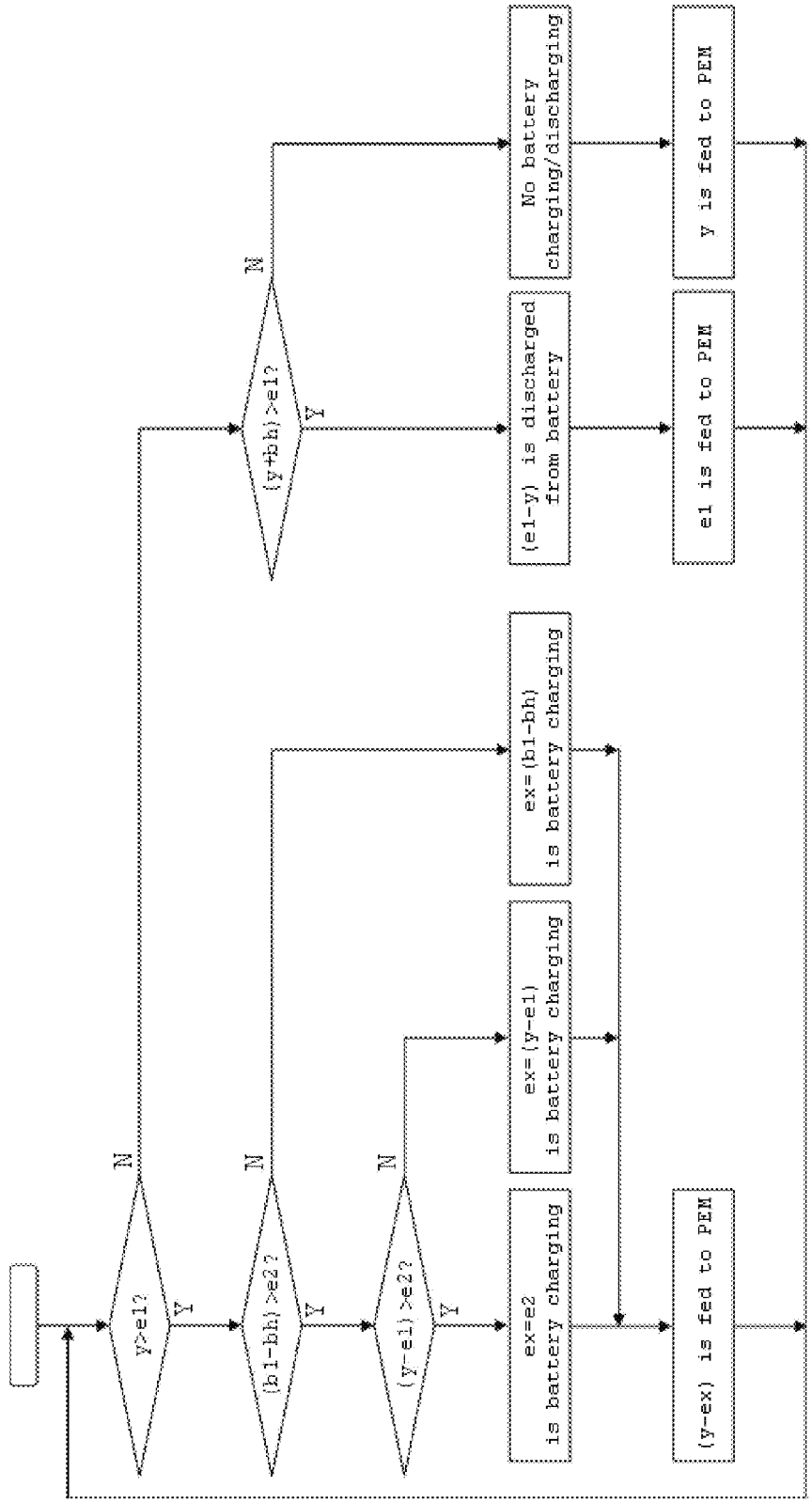
FIG. 30 shows a flowchart of a control algorithm suitably employed in the power generator that constitutes the energy transportation system of the first embodiment of the present invention.

FIG. 30 shows a flowchart of a specific example of an algorithm for the above-described control. That is, when an amount of generated electricity (y) by wind power exceeds a minimum electrolysis load (e1), an excess power (ex) determined by a battery capacity upper limit (e2) specified within the range of 5 to 15% of the wind turbine rating, an upper limit of an operating range value (b1) determined from the battery capacity ratio, and a current battery charge (bh) is exported primarily to the storage battery for charging, a power obtained by subtracting the excess power (ex) from the amount of generated electricity (y) is then fed to the PEM. On the other hand, if the amount of generated electricity (y) of the wind power is less than the minimum electrolysis load (e1), a power is taken from the storage battery and fed to the PEM according to the value of the current battery charge (bh). This eliminates the need to shut down the methane liquefaction facility performing the methane liquefaction process unless an abnormal condition where the wind speed of 3.0 m/s or less continues for more than 20 hours.

Figure 31:
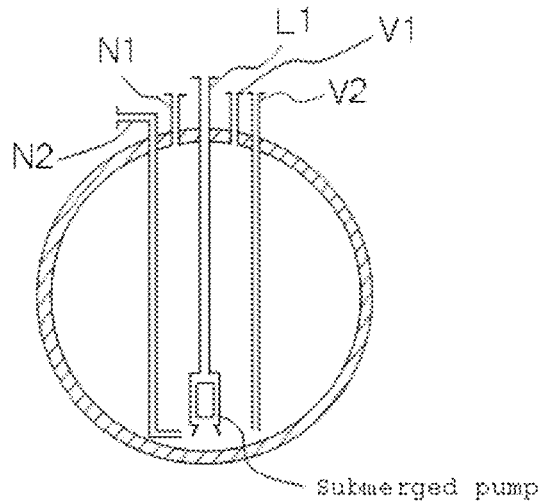
FIG. 31 shows a longitudinal cross-sectional view of a specific example of a spherical tank of the cryogenic tanker of FIG. 20.
Figure 32:
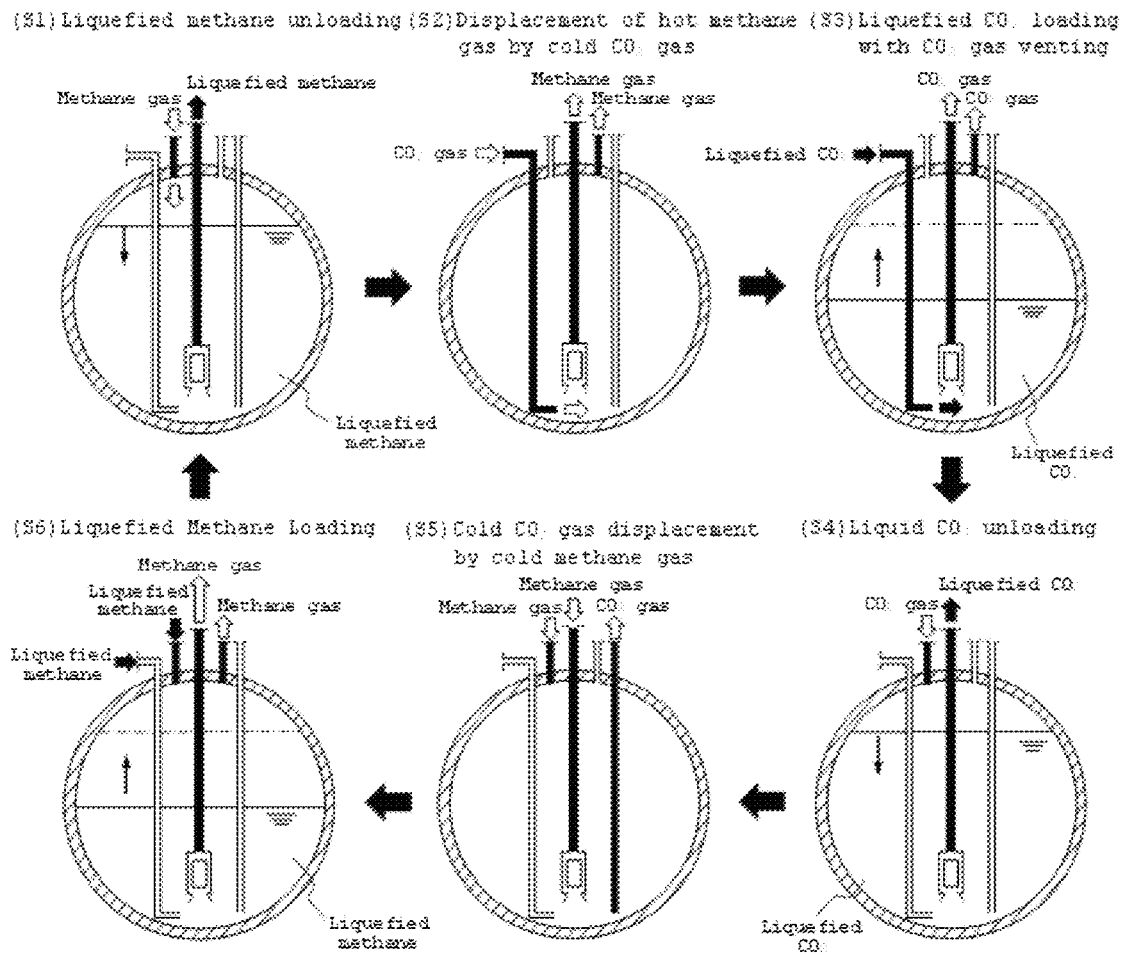
FIG. 32 shows a longitudinal cross-sectional view accompanied by the loading and unloading procedure where use of the cryogenic tanker is shared for the liquefied methane transportation system and the liquefied CO-transportation system, which constitute the energy transportation system of the first embodiment of the present invention.

Next, as mentioned above, the procedure for loading/unloading the liquefied methane and the liquefied $CO_2$ to/from a common cryogenic tanker for transporting the liquefied methane and the liquefied $CO_2$ will be described based on an exemplary case: the storage conditions for the liquefied methane to be handled are a pressure of −0.05 to 0.25 barG and a temperature of −162° C., and the storage conditions for the liquefied $CO_2$ are a pressure of 5.2 to 12.8 barA and a temperature of −56 to −33° C. As shown in FIG. 31, each of a plurality of multiple tanks of the cryogenic tanker has a first feed nozzle N1 with a discharge port at an upper section in the tank, a second feed nozzle N2 with a discharge port at a lower section in the tank, a first vent nozzle V1 with a discharge port at an upper section in tank, a second vent nozzle V2 with a discharge port at a lower section in the tank, and a discharge nozzle Li of a column for a submerged pump. Using these five nozzles, the liquefied methane and the liquefied $CO_2$ can be alternately transported by repeating the following operations S1 to S6, as shown in FIG. 32.

(S1) Liquefied Methane Unloading

The liquefied methane in the spherical tank is unloaded by operating the submerged pump while introducing methane gas at a low temperature of, for example, −50° C. as a displacement gas into the tank from the first feed nozzle N1, and the methane gas is continuously introduced after the unloading is completed to pressurize the tank to, for example, 6.92 barA.

(S2) Displacement of Hot Methane Gas by Cold $CO_2$ Gas

The cold $CO_2$ gas with a pressure of 6.92 barA and a temperature of −50° C., for example, is introduced from a lower section of the tank by the second feed nozzle N2, and methane gas in the tank is vented from the first vent nozzle V1 and the discharge nozzle Li of the submerged pump to replace methane gas with carbon dioxide gas. The density ratio of the methane gas to the $CO_2$ gas at the time of this substitution is 1:2.75.

(S3) Liquefied $CO_2$ Loading with $CO_2$ Gas Venting

The low-temperature liquefied $CO_2$ with a pressure of 6.92 barA and a temperature of −50° C., for example, is introduced from a lower section of the tank by the second feed nozzle N2 for loading, while the $CO_2$ gas in the tank is vented from the first vent nozzle V1 and discharge nozzle Li of the submerged pump to replace $CO_2$ gas with liquid $CO_2$.

(S4) Liquid $CO_2$ Unloading

The liquefied $CO_2$ in the tank is unloaded by operating the submerged pump while introducing low temperature $CO_2$ gas of −50° C., for example, as a replacement gas into the tank from the first feed nozzle N1.

(S5) Displacement of Cold $CO_2$ Gas by Cold Methane Gas

The cold methane gas with a pressure of 6.92 barA and a temperature of −50° C., for example, is introduced from an upper section of the tank and the pump column by the first feed nozzle N1 and the discharge nozzle Li of the submerged pump, while the $CO_2$ gas in the tank is vented from the second vent nozzle V2 to replace the $CO_2$ gas with methane gas. The density ratio of the methane gas to the $CO_2$ gas during this substitution is 1:2.75.

(S6) Liquefied Methane Loading

The liquefied methane is sprayed from an upper section of the tank by the first feed nozzle N1 to cool the tank to a cryogenic temperature of, for example, −130° C., and then the liquefied methane is introduced from the second feed nozzle N2 while venting methane gas from the first vent nozzle V1 and discharge nozzle Li of the submerged pump so as to perform loading with gradual rising of the liquid level from the bottom.

Next, the procedure for loading/unloading the pressurized liquefied methane and the liquefied $CO_2$ will be described based on an exemplary case where the storage conditions for the pressurized liquefied methane to be handled are a pressure of 8.0 to 12.8 barA and a temperature of −120 to −130° C., and the storage conditions for liquefied $CO_2$ are a pressure of 5.2 to 10.8 barA and a temperature of −56 to −33° C.

(S1) Liquefied Methane Unloading

The pressurized liquefied methane in the tank is unloaded by operating the submerged pump while introducing methane gas at a low temperature of, for example, −50° C. as a displacement gas into the tank from the first feed nozzle N1, and the methane gas is continuously introduced after the unloading is completed to pressurize the tank to, for example, 10 barA.

(S2) Displacement of Hot Methane Gas by Cold $CO_2$ Gas

The cold $CO_2$ gas with a pressure of 10 barA and a temperature of −40° C., for example, is introduced from a lower section of the tank by the second feed nozzle N2, and methane gas in the tank is vented through the first vent nozzle V1 and the discharge nozzle Li of the submerged pump to replace the methane gas with carbon dioxide gas. The density ratio of the methane gas to the $CO_2$ gas during this substitution is 1:2.75.

(S3) Liquefied $CO_2$ loading with $CO_2$ gas venting

The low-temperature liquefied $CO_2$ with a pressure of 10 barA and a temperature of −40° C., for example, is introduced from a lower section of the tank by the second feed nozzle N2 for loading, while the $CO_2$ gas in the tank is vented from the first vent nozzle V1 and the discharge nozzle Li of the submerged pump to replace $CO_2$ gas with liquid $CO_2$.

(S4) Liquid $CO_2$ Unloading

The liquefied $CO_2$ in the tank is unloaded by operating the submerged pump while introducing $CO_2$ gas at a low temperature of −40° C., for example, as a replacement gas into the tank from the first feed nozzle N1.

(S5) Displacement of Cold $CO_2$ Gas by Cold Methane Gas

The cold methane gas with a pressure of 10 barA and temperature of −40° C., for example, is introduced from an upper section of the tank and the pump column by the first feed nozzle N1 and the discharge nozzle Li of the submerged pump, while the $CO_2$ gas in the tank is vented from the second vent nozzle V2 to replace the $CO_2$ gas with methane gas. The density ratio of the methane gas to the $CO_2$ gas during this substitution is 1:2.75.

(S6) Liquefied Methane Loading

The liquefied methane is sprayed from an upper section of the tank by the first feed nozzle N1 to cool the tank to a cryogenic temperature of, for example, −90° C., and then the liquefied methane is introduced from the second feed nozzle N2 while venting methane gas from the first vent nozzle V1 and discharge nozzle Li of the submerged pump so as to perform loading with gradual raising of the liquid level from the bottom.

At the liquefied methane receiving terminal, the above-described operation S1 is sequentially performed one by one to the plurality of tanks filled with liquefied methane, and when operation S1 is completed, operations S2 and S3 are continuously performed in each of the plurality of tanks, which can eventually performs unloading of the liquefied methane and loading of the liquefied $CO_2$ in all tanks.

On the other hand, at the methane synthesis site, the above-described operation S4 is sequentially performed one by one to the plurality of tanks filled with the liquefied $CO_2$, and when operation S4 is completed, operations S5 and S6 are continuously performed in each of the plurality of tanks, which can eventually performs unloading of the liquefied $CO_2$ and loading of the liquefied methane in all tanks. The above unloading/loading operations are the same for pressurized liquefied methane.

Figure 33:
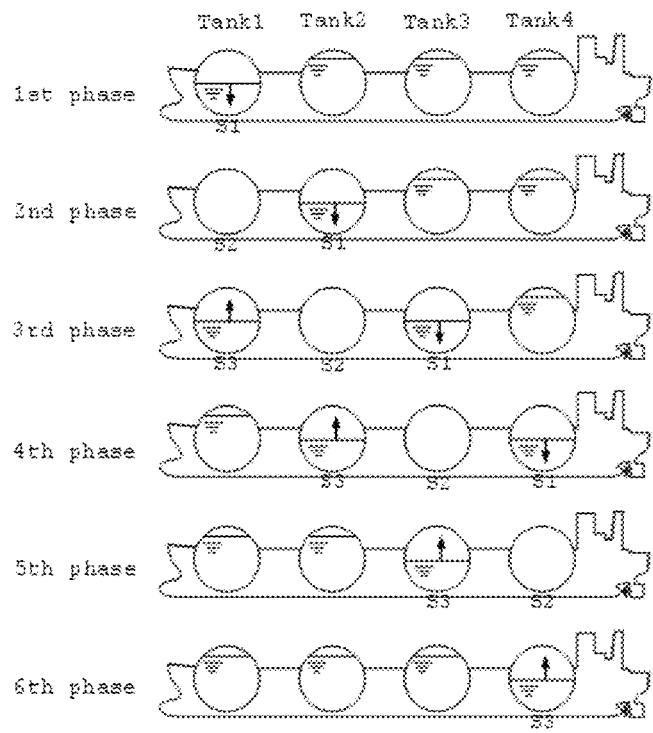
FIG. 33 shows a longitudinal cross-sectional view accompanied by the procedure of replacing liquefied methane with liquefied $CO_2$ in the procedure of FIG. 32, by using a cryogenic tanker with four spherical tanks.

The unloading/loading operations will be specifically described based on a case where a cryogenic tanker has four spherical tanks, at the liquefied methane receiving terminal, as shown in FIG. 33, among these four spherical tanks filled with liquefied methane, operation S1 is performed only on tank 1 in the first phase, and in the second phase, operation S1 is switched from tank 1 to tank 2, and operation S2 is performed on tank 1. In the third phase, operation S1 is switched from tank 2 to 3, operation S2 is switched from tank 1 to 2, and operation S3 is performed in tank 1. In the fourth phase, operation S1 is switched from tank 3 to 4, operation S2 is switched from tank 2 to 3, and operation S3 is performed on tank 2. In the fifth phase, operation S2 is switched from tank 3 to 4 and operation S3 is switched from tank 2 to 3, and in the sixth phase, operation S3 is switched from tank 3 to 4.

Figure 34:
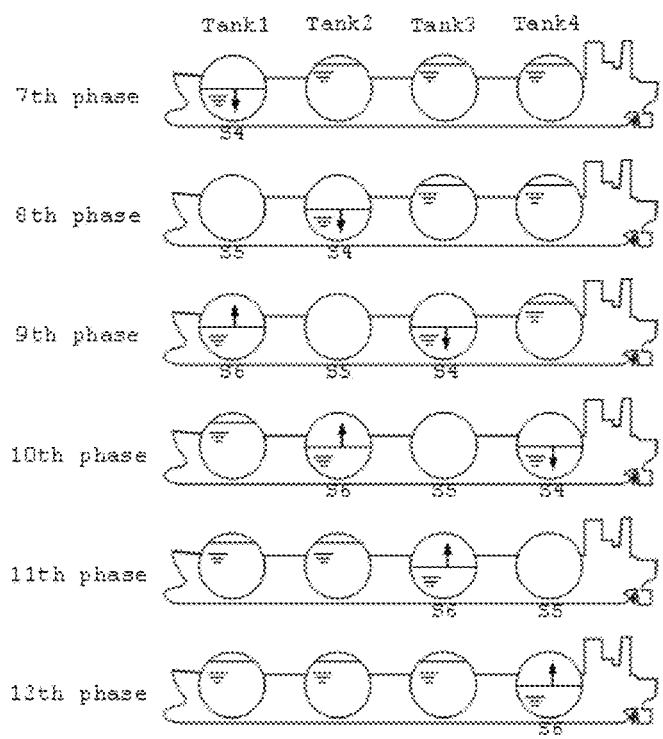
FIG. 34 shows a longitudinal cross-sectional view accompanied by the procedure of replacing liquefied $CO_2$ with liquefied methane in the procedure of FIG. 32 by using a cryogenic tanker with four spherical tanks.

Similarly, at the liquefied methane receiving station, as shown in FIG. 34, among these four spherical tanks filled with liquefied $CO_2$, operation S4 is first performed only on tank 1 in the seventh phase, and in the eighth phase, operation S4 is switched from tank 1 to 2 and operation S5 is performed on tank 1. In the ninth phase, operation S4 is switched from tank 2 to 3, operation S5 is switched from tank 1 to 2, and operation S6 is performed on tank 1. In the tenth phase, operation S4 is switched from tank 3 to 4, operation S5 is switched from tank 2 to 3, and operation S6 is performed in tank 2. In the eleventh phase, operation S5 is switched from tank 3 to 4 and operation S6 is switched from tank 2 to 3, and in the twelfth phase, operation S6 is switched from tank 3 to 4.

It is preferable that an equivalent amount of $CO_2$ emitted into the atmosphere from the entire steps, i.e., from the power generation step to the $CO_2$ transport step described above, is less than 3% of carbon consumed in the entire steps in terms of $CO_2$, and it is more preferable that the equivalent amount of $CO_2$ emitted is less than 1%. In order to offset this preferable equivalent amount of 3% or less of $CO_2$ emission, and more preferable equivalent amount of 1% or less of $CO_2$ emission, it is preferable to use $CO_2$ recovered from the combustion gas of biomass power generation or biomass combustion facilities, or from direct air capture (DAC) as the above-described recycled $CO_2$. This will achieve a zero $CO_2$ emission in the green energy transportation according to the embodiment of the present invention, when these biomass power generation or biomass combustion facilities, or direct air capture is taken into account in the $CO_2$ emissions as a whole.

2. Second Embodiment (Pipeline Transportation System)

2-1 Green Energy Transportation System

The energy transportation system of the first embodiment of the present invention described above includes the marine transportation via cryogenic tankers to transport methane and $CO_2$, but this marine transportation is not required when the PtG complex and the power generation complex are located within the same continent, such as within the Eurasian, North American, and South American continents. In these cases, it is preferable to transport methane gas and $CO_2$ gas in the form of high-pressure gases via pipelines instead of transporting them by cryogenic tankers.

Figure 35:
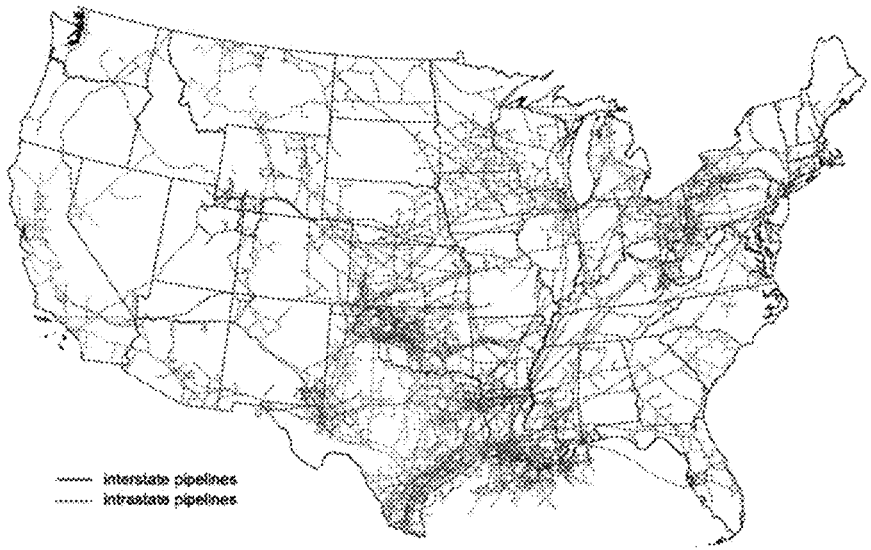
FIG. 35 shows a map of the natural gas pipeline network spread in the United States.

For example, on the North American continent, a network of natural gas pipelines extends across the United States as shown in FIG. 35, and the infrastructure of this natural gas pipeline network may be used to transport methane gas and $CO_2$ gas within the United States. The green energy transportation system according to the second embodiment of the present invention will be thus described hereinbelow in which methane gas and $CO_2$ gas are transported via pipelines. It should be noted that this green energy transportation system using pipelines may be referred to as a green pipeline gas loop.

Figure 36:
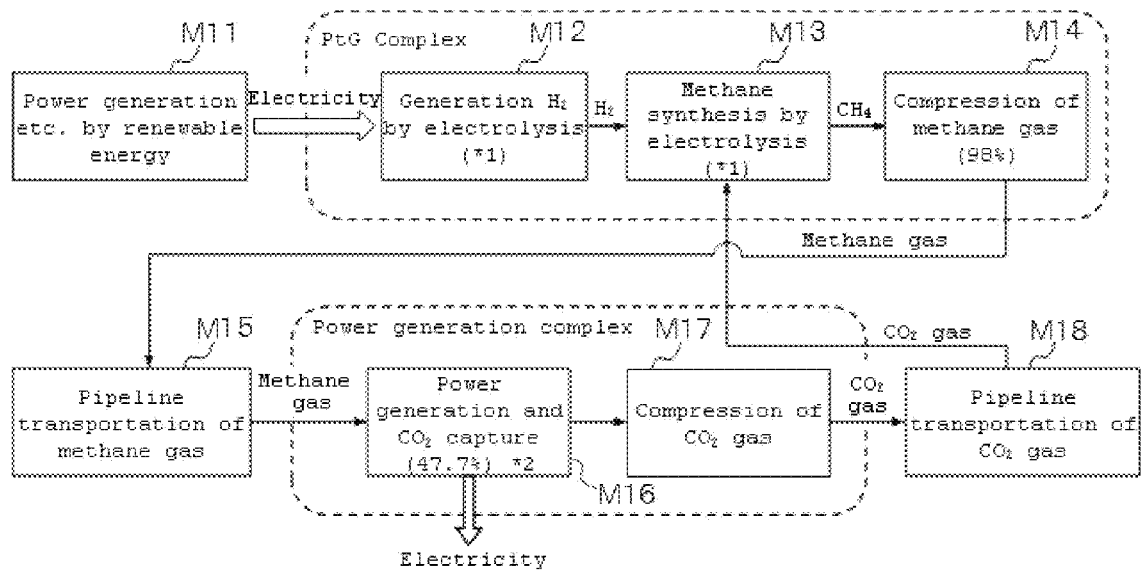
FIG. 36 shows a block flow diagram of the energy transportation system of the second embodiment of the present invention.

As shown in FIG. 36, the energy transportation system of the second embodiment of the present invention includes a power generator M11 using a renewable energy, a hydrogen generator M12, a methane synthesizer M13, a methane gas compression unit M14, a methane transportation system M15, a power generation and carbon capture unit M16, a $CO_2$ gas compression equipment M17, and $CO_2$ transportation system M18. Among the above devices and systems, the power generator M11, hydrogen generator M12, methane synthesizer M13, and power generation and carbon recovery unit M16 are almost the same as the power generator M1, hydrogen generator M2, methane synthesizer M3, and power generation and carbon capture unit M7 of the first embodiment of the present invention described above, respectively, and therefore the following description mainly describe the methane gas compression system M14, the methane transportation system M15, the $CO_2$ gas compression system M17, and the $CO_2$ transportation system M18.

The methane transportation system M15 is a methane gas pipeline that transports methane gas produced by the methane synthesizer M13 from a methane synthesis site to an energy consumption site. In order to maintain the pressure of methane gas flowing inside this methane gas pipeline within the range of about 50 to 125 barA, a methane gas compression system M14 consisting of rotary positive displacement type compressors, each driven by a synchronous motor to which electricity from the renewable energy is supplied as an energy source via an inverter for variable speed motor, are provided at the front end of the methane gas pipeline as the methane transportation system M15 and at one or more relay points located at moderate intervals in the methane gas pipeline. In the subsequent stage of the methane transportation system M15, there is preferably provided a metering machine and a gas composition analyzer to measure the methane gas transported by the methane gas pipeline.

The $CO_2$ transportation system M18 is a $CO_2$ pipeline that transports recycled $CO_2$ collected by the power generation and carbon capture unit M16 from the energy consumption site to the methane synthesis site. As with the methane gas pipeline described above, in order to maintain the pressure of the recycled $CO_2$ flowing inside the $CO_2$ pipeline within the range of about 50 to 125 barA, a $CO_2$ gas compressor M17 consisting of compressors, each driven by a synchronous motor to which electricity from the renewable energy is supplied as an energy source via an inverter for variable speed motors, are installed at the front end of the $CO_2$ pipeline as the $CO_2$ transportation system M18 and at one or more relay points located at moderate intervals in the $CO_2$ pipeline.

The booster compressor for methane gas, which is installed when the pipeline for methane gas is laid over a long distance as described above, is preferably powered by feeding electricity from wind power generation to the VFD for synchronous motors via an extra-high-voltage direct current (HVDC) transmission, but purchased power may also be used to feed electricity to the VFD for synchronous motors. Similarly, the $CO_2$ booster compressor, which is installed when the $CO_2$ pipeline is long, is preferably powered by feeding electricity from wind power generation to the VFD for the synchronous motors via an extra-high-voltage direct current (HVDC) transmission, but purchased power may also be used to feed electricity to the VFD for the synchronous motor.

2-2 Green Energy Transportation Method

Next, an energy transportation method using the energy transportation system of the second embodiment of the present invention described above will be described. The energy transportation method using the energy transportation system of the second embodiment of the present invention includes a power generation step that generates and stores electricity from the renewable energy, a hydrogen generation step that generates hydrogen by electrolysis of water using the power (electricity) obtained in the power generation step, a methane synthesis step that generates methane gas by methanation through a Sabatier reaction using the hydrogen generated in the hydrogen generation step and a recycled $CO_2$ as raw materials, a methane transportation step that transports the methane gas produced in the methane synthesis step to an energy consumption site without emitting $CO_2$ into the atmosphere, a power generation and carbon capture step that generates electricity by a reaction of the methane gas as a feedstock transported by the methane transportation step with oxygen and recovers carbon discharged during the generation of electricity in a form of recycled $CO_2$, and a $CO_2$ transportation step that transports the recycled $CO_2$ recovered in the power generation and carbon capture step to the site where the methane synthesis step is performed without emitting $CO_2$ into the atmosphere.

Of the above series of steps, the methane transportation step includes the transportation step of high-pressure methane gas through a methane gas pipeline extended from the methane synthesis site performing the methane synthesis step to the energy consumption site, in which the high-pressure methane gas is obtained by compressing the methane gas in a rotary positive displacement type compressor driven by a synchronous motor to which electricity from the renewable energy is supplied as an energy source via a variable speed motor inverter. The $CO_2$ transportation step also includes the transportation step of high-pressure recycled $CO_2$ through a $CO_2$ pipeline extended from the energy consumption site to the methane synthesis site, in which the high-pressure recycled $CO_2$ is obtained by compressing the recycled $CO_2$ with a rotary positive displacement type compressor driven by a synchronous motor to which electricity from the renewable energy is supplied as an energy source via a variable speed motor inverter.

In the above methane transportation step, the methane gas may be boosted or pressurized in the middle of the methane gas pipeline by using a methane gas booster compressor driven by a synchronous motor to which electricity from the renewable energy is supplied as an energy source via an ultra-high voltage direct current cable, or electricity is supplied from purchased electricity. Similarly, in the $CO_2$ transportation step, the recycled $CO_2$ may be boosted or pressurized in the middle of the $CO_2$ pipeline by using a $CO_2$ booster compressor driven by a synchronous motor to which electricity from the renewable energy is supplied as an energy source via an ultra-high voltage direct current cable, or electricity is supplied from purchased electricity.

Figure 37:
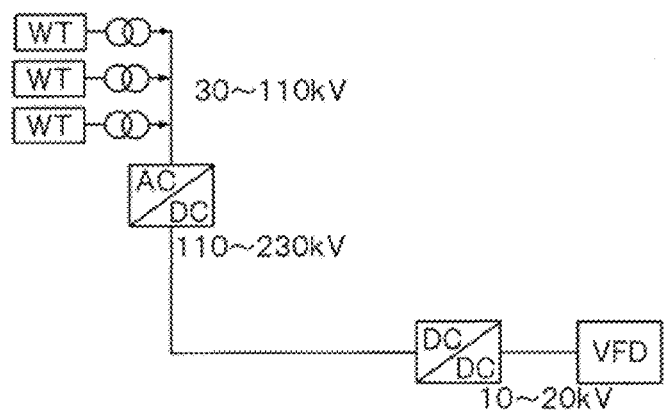
FIG. 37 shows an example of a power distribution diagram for a power generator that constitutes the energy transportation system of the second embodiment of the present invention.

A configuration of the power distribution when using, for example, a wind turbine generator as an energy source of a renewable energy is shown in FIG. 37, in which the output voltage AC 690 V generated by the wind turbine generator (WT) is boosted to 30 to 110 kV by a transformer, and then converted to extra-high-voltage direct current of 110 to 230 kV by an AC-DC converter. This extra-high-voltage direct current is transmitted through an extra-high-voltage current cable, and then stepped down to 10 to 20 kV by a DC-DC converter installed near the synchronous motor.

CLAUSES (Clause 1)

A green energy transportation system comprising: a power generator that generates and stores electricity from a renewable energy; a hydrogen generator that generates hydrogen by electrolysis of water using the electricity obtained from the power generator; a methane synthesizer that generates methane by a Sabatier reaction using the hydrogen generated by the hydrogen generator and a recycled $CO_2$ as raw materials; a methane transportation system that transports the methane produced in the methane synthesizer to an energy consumption site without emitting $CO_2$ into an atmosphere; a power generation and carbon capture unit that generates electricity by reacting the methane transported by the methane transportation system with oxygen, and recovers carbon discharged during the generation of electricity as recycled $CO_2$; and a $CO_2$ transportation system that transports the recycled $CO_2$ to a methane synthesis site where the methane synthesizer is installed without emitting $CO_2$ into an atmosphere.

(Clause 2)
The green energy transportation system according to clause 1, wherein the electrolysis by the hydrogen generator is performed by a solid oxide water electrolysis apparatus, a solid polymer water electrolysis apparatus, or an alkaline water electrolysis apparatus.

(Clause 3)
The green energy transportation system according to clause 1, wherein the hydrogen generator has a hydrogen storage system to store the generated hydrogen.

(Clause 4)
The green energy transportation system according to clause 1, wherein an excess amount of hydrogen as the raw material is introduced into a reactor of the methane synthesizer in a range of 4.05 to 7.00 moles relative to a stoichiometric amount of 4 moles.

(Clause 5)
The green energy transportation system according to clause 4, wherein the methane synthesizer has a reverse water gas shift reactor that produces carbon monoxide from the raw materials of the hydrogen and the recycled $CO_2$ immediately before the reactor that performs the Sabatier reaction.

(Clause 6)
The green energy transportation system according to clause 1, wherein the power generation by the power generation and carbon capture unit is selected from a combined cycle, a solid oxide fuel cell, or an Allam cycle with an oxygen plant and a carbon dioxide cycle.

(Clause 7)
The green energy transportation system according to clause 1 further comprising: a methane liquefaction unit that liquefies the methane by using a rotary positive displacement type refrigerant compressor driven by a synchronous motor to which electricity from a renewable energy is supplied as an energy source via a variable speed motor inverter so as to transport the methane generated in the methane synthesizer in a form of liquid; a liquefied methane receiving and regasifying unit that regasifies the liquid methane transported by the methane transportation system after receiving it into a liquefied methane storage tank such that the methane transportation system transports the liquefied methane liquefied by the methane liquefaction unit to an energy consumption site by a liquefied methane tanker driven by a first power unit without emitting $CO_2$ to an atmosphere; a $CO_2$ liquefaction unit that liquefies the recycled $CO_2$ recovered in the power generation and carbon capture unit so as to transport the recycled $CO_2$ in a form of liquid; and a liquefied $CO_2$ receiving and regasifying unit that regasifies the liquefied $CO_2$ transported by the $CO_2$ transportation system after received it into a liquefied $CO_2$ storage tank such that the $CO_2$ transportation system transports the liquefied $CO_2$ obtained in the $CO_2$ liquefaction unit to the methane synthesis site where the methane synthesizer is installed by a liquefied $CO_2$ tanker driven by a second power unit without emitting $CO_2$ into a atmosphere
wherein the methane liquefaction unit and the liquefied methane receiving and regasifying unit are respectively provided before and after the methane transportation system, and the $CO_2$ liquefaction unit and the liquefied $CO_2$ receiving and regasifying unit are respectively provided before and after the $CO_2$ transportation system.

(Clause 8)
The green energy transportation system according to clause 7, wherein each of the first power unit and the second power unit is either a rechargeable battery or an internal combustion engine fueled by hydrogen or liquefied methane.

(Clause 9)
The green energy transportation system according to clause 7, wherein the methane liquefaction unit has a stripper that flushes the liquefied methane under a pressure of 0.8 to 2.0 barA and a temperature of −170 to −180° C., and a non-liquefied hydrogen produced by the stripper is recycled to the methane synthesizer and reused as a raw material.

(Clause 10)
The green energy transportation system according to clause 8, wherein the methane liquefaction unit has a heat exchanger to exchange heat between methane and refrigerant, and the heat exchanger is designed that a flow rate of methane containing the non-liquefied hydrogen is ensured to have at least 20% of a design flow rate.

(Clause 11)
The green energy transportation system according to clause 6, wherein the $CO_2$ liquefaction unit includes a compressor that compresses the recycled $CO_2$ recovered in the power generation and carbon capture unit to a pressure of 45 to 80 barA and a heat exchanger that cools the recycled $CO_2$ for liquefaction to a temperature of −33 to −56° C. by using a cold heat from regasification of the liquefied methane of a pressure of 10 to 100 barA.

(Clause 12)
The green energy transportation system according to clause 11, wherein the $CO_2$ liquefaction unit further includes a liquid turbine that recovers power by depressurizing the liquefied $CO_2$, which is liquefied by the heat exchanger, to a pressure of 5.2 to 12.8 barA.

(Clause 13)
The green energy transportation system according to clause 11, wherein the $CO_2$ liquefaction unit further includes an insulated spherical storage tank that stores the liquefied $CO_2$ at a pressure of 5.2 to 12.8 barA and a temperature of −56 to −33° C.

(Clause 14)
The green energy transportation system according to clause 1, wherein the methane transportation system includes a methane gas pipeline that transports a methane gas produced by the methane synthesizer to an energy consumption site, and methane gas compressors installed at a front end and a relay point of the methane gas pipeline each consisting of a rotary positive displacement type driven by a synchronous motor to which electricity from the renewable energy is supplied as an energy source via a variable speed motor inverter so as to maintain a pressure of the methane gas flowing inside the methane gas pipeline in a range of 50 to 125 barA, and
the $CO_2$ transportation system includes a $CO_2$ pipeline that transports the recycled $CO_2$ recovered from the power generation and carbon capture unit to the methane synthesis site, and $CO_2$ gas compressors installed at a front end and a relay point of the $CO_2$ pipeline each driven by a synchronous motor to which electricity from the renewable energy as an energy source is supplied via a variable speed motor inverter so as to maintain a pressure of the recovered recycled $CO_2$ flowing inside the $CO_2$ pipeline in a range of 50 to 125 barA.

(Clause 15)
A green energy transportation method comprising: a power generation step that generates and stores electricity from a renewable energy; a hydrogen generation step that generates hydrogen by electrolysis of water using electricity obtained in the power generation unit; a methane synthesis step that generates methane by a Sabatier reaction using the hydrogen generated in the hydrogen generation step and a recycled $CO_2$ as raw materials; a methane transportation step that transports the methane produced in the methane synthesis step to an energy consumption site without emitting $CO_2$ into an atmosphere; a power generation and carbon capture step that generates electricity by reacting the methane transported by the methane transportation step with oxygen, and recovers carbon discharged during the generation of electricity in a form of recycled $CO_2$; and a $CO_2$ transportation step that transports the recycled $CO_2$ to a site where the methane synthesis step is performed without emitting $CO_2$ into an atmosphere.

(Clause 16)

The green energy transportation method according to clause 15, wherein a part of the hydrogen generated by the electrolysis of water is stored such that a fixed amount of hydrogen is supplied as a raw material to the methane synthesis step.

(Clause 17)

The green energy transportation method according to clause 15, wherein the power generation by the renewable energy is performed by a wind turbine generator equipped with a storage battery, and the storage battery is set to have a capacity value in a range of 106 to 126% of a wind turbine rating of the wind turbine, and the storage battery is operated in an operational range of 20 to 90% of the wind turbine rating.

(Clause 18)

The green energy transportation method as claimed in clause 17, wherein the electrolysis of water in the hydrogen generation step is set to have a minimum electrolysis load, which is a power required for the electrolysis of water, within a range of 5 to 30% of the wind turbine rating, and if a generated power by the wind turbine, whose variable is the wind speed, is less than the minimum electrolysis load, its shortage is made up from the storage battery, and if the generated power is equal to or above the minimum electrolysis load, the generated power is used for the electrolysis of water, and an excess power of the generated power over the minimum electrolysis load is charged to the storage battery under conditions below an upper limit set within a range of 5 to 15% of the wind turbine rating and within the operational range of the storage battery.

(Clause 19)

The green energy transportation method according to clause 18 further comprising: a methane liquefaction step that liquefies the methane using a rotary positive displacement type refrigerant compressor driven by a synchronous motor to which electricity from the renewable energy is supplied as an energy source via a variable speed motor inverter; a liquefied methane receiving and regasifying step that regasifies the liquefied methane after receiving it into a liquefied methane storage tank such that the methane transportation step transports the liquefied methane liquefied by the methane liquefaction unit to an energy consumption site by a liquefied methane tanker driven by a first power unit without emitting $CO_2$ to an atmosphere; a $CO_2$ liquefaction step that liquefies the recycled $CO_2$; and a liquefied $CO_2$ receiving and regasifying unit that regasifies the liquefied $CO_2$ transported by the $CO_2$ transportation step after received in a liquefied $CO_2$ storage tank such that the $CO_2$ transportation step transports the liquefied $CO_2$ liquefied in the $CO_2$ liquefaction step to the methane synthesis site where the methane synthesis step is performed by a liquefied $CO_2$ tanker driven by a second power unit without emitting $CO_2$ to an atmosphere wherein the methane liquefaction step and the liquefied methane receiving and regasifying step are respectively provided before and after said methane transportation step, and the $CO_2$ liquefaction step and the liquefied $CO_2$ receiving and regasifying unit are respectively provided before and after the $CO_2$ transportation step.

(Clause 20)

The green energy transportation method according to clause 19, wherein the wind turbine generator is a permanent magnet synchronous generator, and the AC voltage generated by the wind turbine generator is boosted to 30 to 110 kV by a transformer and then converted to a DC power having DC voltage of 10 to 20 kV and DC current of 5.0 to 10.0 kA by an AC-DC converter, and the DC power is fed to an electrolyzer that performs the electrolysis of water via a DC-DC converter consisting of a solid-state transformer to step down to 100 to 150V as well as fed to the synchronous motor that drives the refrigerant compressor.

(Clause 21)

The green energy transportation method according to clause 19, wherein dedicated cryogenic tankers are respectively used for the liquefied methane transportation and the liquefied $CO_2$ transportation, and when the liquefied $CO_2$ to be transported has a pressure of 5.2 to 12.8 barA and a temperature of −56 to −33° C., the cryogenic tanker for the liquefied $CO_2$ is equipped with 3 to 7 spherical tanks or 4 to 8 horizontal cylindrical tanks, and material of the tanks is aluminum-killed carbon steel, 1.5% Ni nickel steel, or high tensile nickel steel for low temperature service.

(Clause 22)

The green energy transportation method according to clause 19, wherein the cryogenic tanker for liquefied methane is a Moss type with 3 to 7 spherical tanks, and when the liquefied methane to be transported has a pressures of −0.05 to 0.25 barG and a temperature of −162° C., material of the tanks is 6-7.5% Ni steel, 8.5-9.5% Ni steel, 18-8 stainless steel, or aluminum alloy 5083, and when the liquefied methane has pressures of 8.0 to 12.8 barA and temperatures of −120 to −130° C., material of the tanks is −7.5% Ni steel, 8.5-9.5% Ni steel, 18-8 stainless steel, aluminum alloy 5083, or 5% Ni steel.

(Clause 23)

The green energy transportation method according to clause 19, wherein the methane transportation step transports a liquefied methane at a pressure of −0.05 to 0.25 barG and a temperature of −162° C., and the $CO_2$ transportation step transports liquefied $CO_2$ at a pressure of 5.2 to 12.8 barA and a temperature of −56 to −33° C., and a common cryogenic tanker with 3 to 7 spherical tanks or 4 to 8 horizontal cylindrical tanks is shared for transportation of the liquefied methane and the liquefied $CO_2$, where material of the tanks is 6-7.5% Ni steel, 8.5-9.5% Ni steel, 18-8 stainless steel, or aluminum alloy 5083.

(Clause 24)

The green energy transportation method according to clause 19, wherein the methane transportation step transports a pressurized liquefied methane at a pressure of 8.0 to 12.8 barA and a temperature of −120 to −130° C., and the $CO_2$ transportation step transports a liquefied $CO_2$ at a pressure of 5.2 to 10.8 barA and a temperature of −56 to −33° C., and a common cryogenic tanker with 3 to 7 spherical tanks or 4 to 8 horizontal cylindrical tanks is shared for transportation of the pressurized liquefied methane and the liquefied $CO_2$, where material of the tanks is 6-7.5% Ni steel, 8.5-9.5% Ni steel, 18-8 stainless steel, aluminum alloy 5083, or 5% Ni steel.

(Clause 25)

The green energy transportation method according to clause 24, wherein the pressurized liquefied methane is produced by exchanging heat of a pre-pressurized methane gas with a refrigerant for cooling, followed by flushing to partially depressurize to a pressure of 8.0 to 12.8 barA by using an expansion mechanism.

(Clause 26)

The green energy transportation method according to clause 23 or 24, wherein each of the tanks on the cryogenic tanker has a first feed nozzle with a discharge outlet at an upper section in the tank, a second feed nozzle with a discharge outlet at a lower section in the tank, a first vent nozzle with a discharge outlet at an upper section of the tank, a second vent nozzle with a discharge outlet at a lower section of the tank, and a discharge nozzle of a column for a submerged pump, and the liquefied methane and the liquefied $CO_2$ are alternately transported by repeating the following operations S1 to S6 using these five nozzles:

(S1) Liquefied methane in the tank is unloaded by operating the submerged pump while introducing low-temperature methane gas as a displacement gas into the tank from the first feed nozzle, and then pressurizing the tank by continuously introducing the methane gas after the unloading is completed.

(S2) Low-temperature $CO_2$ gas is introduced from a lower section of the tank through the second feed nozzle, and the methane gas in the tank is vented through the first vent nozzle and the discharge nozzle of the submerged pump to replace the methane gas with the $CO_2$ gas.

(S3) Low-temperature liquefied $CO_2$ is introduced from a lower section of the tank by the second feed nozzle for loading, and the $CO_2$ gas in the tank is vented from the first vent nozzle and the discharge nozzle of the submerged pump to replace the $CO_2$ gas with the liquid $CO_2$.

(S4) Liquid $CO_2$ in the tank is unloaded by operating the submerged pump while introducing low-temperature $CO_2$ gas into the tank as the replacement gas from the first feed nozzle.

(S5) Low-temperature methane gas is introduced from an upper section of the tank and the pump column by the first feed nozzle and the discharge nozzle of the submerged pump, and the $CO_2$ gas in the tank is vented from the second vent nozzle to replace the $CO_2$ gas with the methane gas.

(S6) Liquefied methane is sprayed from an upper section of the tank by the first feed nozzle to cool the spherical tank to a very low temperature, and then liquefied methane is introduced from the second feed nozzle while venting methane gas from the first vent nozzle and the discharge nozzle of the submerged pump so as to perform loading with gradual rising of a liquid level.

(Clause 27)

The green energy transportation method according to clause 26, wherein the operation S1 is sequentially performed to the tanks filled with the liquefied methane one by one, and when the operation S1 is completed, the operations S2 and S3 are continuously performed in each of the tanks, which eventually performs unloading of the liquefied methane and loading of the liquefied $CO_2$ in all the tanks at a liquefied methane receiving site, whereas the operation S4 is sequentially performed to the tanks filled with the liquefied $CO_2$ one by one, and when the operation S4 is completed, the operations S5 and S6 are continuously performed in each of the tanks which eventually performs unloading of the liquefied $CO_2$ and loading of the liquefied methane in all the tanks at the methane synthesis site.

(Clause 28)

The green energy transportation method according to clause 15, wherein the methane transportation step uses a methane gas pipeline extended from the methane synthesis site where the methane synthesis step is performed to an energy consumption site to transport a high-pressure methane gas obtained by compressing the methane by a rotary positive displacement type compressor driven by a synchronous motor to which electricity from the renewable energy as an energy source is supplied via a variable speed motor inverter, and the $CO_2$ transport step uses a $CO_2$ pipeline extended from the energy consumption site to the methane synthesis site to transport a high-pressure recycled $CO_2$ obtained by compressing the recycled $CO_2$ with a rotary positive displacement type compressor driven by a synchronous motor to which electricity from the renewable energy as an energy source is supplied via a variable speed motor inverter.

(Clause 29)

The green energy transportation method according to clause 28, wherein the methane transportation step includes a methane gas pressurize step in a middle of the methane gas pipeline which uses a booster compressor for methane gas driven by a synchronous motor to which electricity is supplied from a purchased electricity or from the renewable energy as an energy source via an ultra-high voltage direct current cable, and the $CO_2$ transportation step includes a recycled $CO_2$ pressurize step in the middle of the $CO_2$ pipeline by using a booster compressor for $CO_2$ driven by a synchronous motor to which electricity is supplied from a purchased electricity or from the renewable energy as an energy source via an ultra-high voltage direct current cable.

(Clause 30)

The green energy transportation method according to clause 15, wherein an equivalent amount of $CO_2$ emission to an atmosphere is equal to or less than 3% of carbon consumed in the entire steps from the power generation step to the $CO_2$ transportation step.

(Clause 31)

The green energy transportation method according to clause 30, wherein $CO_2$ recovered from a biomass power generation or a combustion gas of biomass combustion facilities or $CO_2$ recovered from direct air capture is used as the recycled $CO_2$ to offset the 3% or less of the $CO_2$ emissions.

REFERENCE NUMERALS LIST

1 Wind turbine generators
2 Power collection system
3 Transmission lines
4 Substation
10*a* Low-pressure screw compressor
10*b* High-pressure screw compressor
11 High-pressure hydrogen storage facility
12 Primary piping
13 Manifold
14 Storage piping group
20 Reverse water gas shift reactor
21, 22, 23, 24 Methane synthesis reactor 25, 26, 27, 28, 29 Cooler
30 Carbon dioxide removal system
31, 41 First heat exchanger
32, 42 Second heat exchanger
33, 43 Third heat exchanger
34 Propane multi-stage compressor
35 Dryer
36 Scrub column
37a, 37b, 37c MR compressor
38 Main low-temperature heat exchanger
39, 47, 55 Flash drum
44 Propane compressor
45 Ethylene compressor
46 Methane compressor
51, 52 Compressors
53 Expander
54 Heat exchanger
61 Pressurized heat exchanger
62 Expansion mechanism
63 Cooling system
71 Unloading arm
72 Unloading line
73 Liquefied methane tank
74 First pump
75a Second pump
75b Booster pump
76a High pressure vaporizer
76b Low-pressure vaporizer
77 Return gas blower
78 BOG compressor
81 Compressor
82 Gas turbine
83 Waste heat recovery boiler
84 HP turbine
85 IP turbine
86 LP turbine
87 Carbon recovery unit
91 Absorption column
92 Reboiler
93 Regeneration column
94 Circulation system
101 Reformer
102 Fuel cell
103 Condenser
111 Turbine
112 Heat exchanger
113 Compressor
121 Compressor
122 Heat exchanger
123 Liquid turbine
124 Spherical storage tank
Li Discharge nozzle
N1 First feed nozzle
N2 Second feed nozzle
V1 First vent nozzle
V2 Second vent nozzle
T Cryogenic tanker

The invention claimed is:

1. A green energy transportation system comprising: a power generator that generates and stores electricity from a renewable energy; a hydrogen generator that generates hydrogen by electrolysis of water using the electricity obtained from the power generator; a methane synthesizer that generates methane by a Sabatier reaction using the hydrogen generated by the hydrogen generator and a recycled $CO_2$ as raw materials; a methane transportation system that transports the methane produced in the methane synthesizer to an energy consumption site without emitting $CO_2$ into an atmosphere; a power generation and carbon capture unit that generates electricity by reacting the methane transported by the methane transportation system with oxygen, and recovers carbon discharged during the generation of electricity as recycled $CO_2$; and a $CO_2$ transportation system that transports the recycled $CO_2$ to a methane synthesis site where the methane synthesizer is installed without emitting $CO_2$ into an atmosphere.

2. The green energy transportation system according to claim 1, wherein the electrolysis by the hydrogen generator is performed by a solid oxide water electrolysis apparatus, a solid polymer water electrolysis apparatus, or an alkaline water electrolysis apparatus.

3. The green energy transportation system according to claim 1, wherein the hydrogen generator has a hydrogen storage system to store the generated hydrogen.

4. The green energy transportation system according to claim 1, wherein an excess amount of hydrogen as the raw material is introduced into a reactor of the methane synthesizer in a range of 4.05 to 7.00 moles relative to a stoichiometric amount of 4 moles.

5. The green energy transportation system according to claim 4, wherein the methane synthesizer has a reverse water gas shift reactor that produces carbon monoxide from the raw materials of the hydrogen and the recycled $CO_2$ immediately before the reactor that performs the Sabatier reaction.

6. The green energy transportation system according to claim 1, wherein the power generation by the power generation and carbon capture unit is selected from a combined cycle, a solid oxide fuel cell, or an Allam cycle with an oxygen plant and a carbon dioxide cycle.

7. The green energy transportation system according to claim 1 further comprising: a methane liquefaction unit that liquefies the methane by using a rotary positive displacement type refrigerant compressor driven by a synchronous motor to which electricity from the renewable energy is supplied as an energy source via a variable speed motor inverter so as to transport the methane generated in the methane synthesizer in a form of liquid; a liquefied methane receiving and regasifying unit that regasifies the liquid methane transported by the methane transportation system after receiving it into a liquefied methane storage tank such that the methane transportation system transports the liquefied methane liquefied by the methane liquefaction unit to an energy consumption site by a liquefied methane tanker driven by a first power unit without emitting $CO_2$ to an atmosphere; a $CO_2$ liquefaction unit that liquefies the recycled $CO_2$ recovered in the power generation and carbon capture unit so as to transport the recycled $CO_2$ in a form of liquid; and a liquefied $CO_2$ receiving and regasifying unit that regasifies the liquefied $CO_2$ transported by the $CO_2$ transportation system after received it into a liquefied $CO_2$ storage tank such that the $CO_2$ transportation system transports the liquefied $CO_2$ obtained in the $CO_2$ liquefaction unit to the methane synthesis site where the methane synthesizer is installed by a liquefied $CO_2$ tanker driven by a second power unit without emitting $CO_2$ into a atmosphere
wherein the methane liquefaction unit and the liquefied methane receiving and regasifying unit are respectively provided before and after the methane transportation system, and the $CO_2$ liquefaction unit and the liquefied $CO_2$ receiving and regasifying unit are respectively provided before and after the $CO_2$ transportation system.

8. The green energy transportation system according to claim 7, wherein each of the first power unit and the second power unit is either a rechargeable battery or an internal combustion engine fueled by hydrogen or liquefied methane.

9. The green energy transportation system according to claim 7, wherein the methane liquefaction unit has a stripper that flushes the liquefied methane under a pressure of 0.8 to 2.0 barA and a temperature of −170 to −180° C., and a non-liquefied hydrogen produced by the stripper is recycled to the methane synthesizer and reused as a raw material.

10. The green energy transportation system according to claim 8, wherein the methane liquefaction unit has a heat exchanger to exchange heat between methane and refrigerant, and the heat exchanger is designed that a flow rate of methane containing the non-liquefied hydrogen is ensured to have at least 20% of a design flow rate.

11. The green energy transportation system according to claim 6, wherein the $CO_2$ liquefaction unit includes a compressor that compresses the recycled $CO_2$ recovered in the power generation and carbon capture unit to a pressure of 45 to 80 barA and a heat exchanger that cools the recycled $CO_2$ for liquefaction to a temperature of −33 to −56° C. by using a cold heat from regasification of the liquefied methane of a pressure of 10 to 100 barA.

12. The green energy transportation system according to claim 11, wherein the $CO_2$ liquefaction unit further includes a liquid turbine that recovers power by depressurizing the liquefied $CO_2$, which is liquefied by the heat exchanger, to a pressure of 5.2 to 12.8 barA.

13. The green energy transportation system according to claim 11, wherein the $CO_2$ liquefaction unit further includes an insulated spherical storage tank that stores the liquefied $CO_2$ at a pressure of 5.2 to 12.8 barA and a temperature of −56 to −33° C.

14. The green energy transportation system according to claim 1, wherein the methane transportation system includes a methane gas pipeline that transports a methane gas produced by the methane synthesizer to an energy consumption site, and methane gas compressors installed at a front end and a relay point of the methane gas pipeline each consisting of a rotary positive displacement type driven by a synchronous motor to which electricity from the renewable energy is supplied as an energy source via a variable speed motor inverter so as to maintain a pressure of the methane gas flowing inside the methane gas pipeline in a range of 50 to 125 barA, and the $CO_2$ transportation system includes a $CO_2$ pipeline that transports the recycled $CO_2$ recovered from the power generation and carbon capture unit to the methane synthesis site, and $CO_2$ gas compressors installed at a front end and a relay point of the $CO_2$ pipeline each driven by a synchronous motor to which electricity from the renewable energy as an energy source is supplied via a variable speed motor inverter so as to maintain a pressure of the recovered recycled $CO_2$ flowing inside the $CO_2$ pipeline in a range of 50 to 125 barA.

15. A green energy transportation method comprising: a power generation step that generates and stores electricity from a renewable energy; a hydrogen generation step that generates hydrogen by electrolysis of water using electricity obtained in the power generation unit; a methane synthesis step that generates methane by a Sabatier reaction using the hydrogen generated in the hydrogen generation step and a recycled $CO_2$ as raw materials; a methane transportation step that transports the methane produced in the methane synthesis step to an energy consumption site without emitting $CO_2$ into an atmosphere; a power generation and carbon capture step that generates electricity by reacting the methane transported by the methane transportation step with oxygen, and recovers carbon discharged during the generation of electricity in a form of recycled $CO_2$; and a $CO_2$ transportation step that transports the recycled $CO_2$ to a site where the methane synthesis step is performed without emitting $CO_2$ into an atmosphere.

16. The green energy transportation method according to claim 15, wherein a part of the hydrogen generated by the electrolysis of water is stored such that a fixed amount of hydrogen is supplied as a raw material to the methane synthesis step.

17. The green energy transportation method according to claim 15, wherein the power generation by the renewable energy is performed by a wind turbine generator equipped with a storage battery, and the storage battery is set to have a capacity value in a range of 106 to 126% of a wind turbine rating of the wind turbine, and the storage battery is operated in an operational range of 20 to 90% of the wind turbine rating.

18. The green energy transportation method as claimed in claim 17, wherein the electrolysis of water in the hydrogen generation step is set to have a minimum electrolysis load, which is a power required for the electrolysis of water, within a range of 5 to 30% of the wind turbine rating, and if a generated power by the wind turbine, whose variable is the wind speed, is less than the minimum electrolysis load, its shortage is made up from the storage battery, and if the generated power is equal to or above the minimum electrolysis load, the generated power is used for the electrolysis of water, and an excess power of the generated power over the minimum electrolysis load is charged to the storage battery under conditions below an upper limit set within a range of 5 to 15% of the wind turbine rating and within the operational range of the storage battery.

19. The green energy transportation method according to claim 18 further comprising: a methane liquefaction step that liquefies the methane using a rotary positive displacement type refrigerant compressor driven by a synchronous motor to which electricity from the renewable energy is supplied as an energy source via a variable speed motor inverter; a liquefied methane receiving and regasifying step that regasifies the liquefied methane after receiving it into a liquefied methane storage tank such that the methane transportation step transports the liquefied methane liquefied by the methane liquefaction unit to an energy consumption site by a liquefied methane tanker driven by a first power unit without emitting $CO_2$ to an atmosphere; a $CO_2$ liquefaction step that liquefies the recycled $CO_2$; and a liquefied $CO_2$ receiving and regasifying unit that regasifies the liquefied $CO_2$ transported by the $CO_2$ transportation step after received in a liquefied $CO_2$ storage tank such that the $CO_2$ transportation step transports the liquefied $CO_2$ liquefied in the $CO_2$ liquefaction step to the methane synthesis site where the methane synthesis step is performed by a liquefied $CO_2$ tanker driven by a second power unit without emitting $CO_2$ to an atmosphere wherein the methane liquefaction step and the liquefied methane receiving and regasifying step are respectively provided before and after said methane transportation step, and the $CO_2$ liquefaction step and the liquefied $CO_2$ receiving and regasifying unit are respectively provided before and after the $CO_2$ transportation step.

20. The green energy transportation method according to claim 15, wherein the methane transportation step uses a methane gas pipeline extended from the methane synthesis site where the methane synthesis step is performed to an energy consumption site to transport a high-pressure methane gas obtained by compressing the methane by a rotary positive displacement type compressor driven by a synchronous motor to which electricity from the renewable energy as an energy source is supplied via a variable speed motor inverter, and the $CO_2$ transport step uses a $CO_2$ pipeline extended from the energy consumption site to the methane synthesis site to transport a high-pressure recycled $CO_2$ obtained by compressing the recycled $CO_2$ with a rotary positive displacement type compressor driven by a synchronous motor to which electricity from the renewable energy as an energy source is supplied via a variable speed motor inverter.

\* \* \* \* \*